US012575880B2

(12) United States Patent
Harlev et al.

(10) Patent No.: US 12,575,880 B2
(45) Date of Patent: Mar. 17, 2026

(54) SYSTEMS FOR CARDIAC ABLATION AND ASSOCIATED METHODS

(71) Applicant: Affera, Inc., Newton, MA (US)

(72) Inventors: Doron Harlev, Watertown, MA (US); Paul B. Hultz, Watertown, MA (US)

(73) Assignee: AFFERA, INC., Newton, MA (US)

( * ) Notice: Subject to any disclaimer, the term of this patent is extended or adjusted under 35 U.S.C. 154(b) by 580 days.

(21) Appl. No.: 18/061,378

(22) Filed: Dec. 2, 2022

(65) Prior Publication Data

US 2023/0157751 A1 May 25, 2023

Related U.S. Application Data

(63) Continuation of application No. 17/600,523, filed as application No. PCT/US2021/014216 on Jan. 20, 2021, now Pat. No. 11,553,962.

(Continued)

(51) Int. Cl.
*A61B 18/12* (2006.01)
*A61B 5/00* (2006.01)
(Continued)

(52) U.S. Cl.
CPC .......... *A61B 18/1492* (2013.01); *A61B 5/287* (2021.01); *A61B 5/367* (2021.01);
(Continued)

(58) Field of Classification Search
CPC . A61B 18/1442; A61B 18/1206; A61B 34/25; A61B 2018/0212;
(Continued)

(56) References Cited

U.S. PATENT DOCUMENTS

| | | | |
|---|---|---|---|
| 4,708,145 | A | 11/1987 | Tacker, Jr. et al. |
| 5,010,894 | A | 4/1991 | Edhag |
| | | (Continued) | |

FOREIGN PATENT DOCUMENTS

| | | |
|---|---|---|
| JP | 2014519367 A | 8/2014 |
| WO | 1999/060923 A1 | 12/1999 |
| WO | 2019/0157285 A1 | 8/2019 |

OTHER PUBLICATIONS

Japanese Patent Application No. 2022-544719; Office Action dated Jul. 10, 2024; 8 pgs.

(Continued)

*Primary Examiner* — Daniel W Fowler
(74) *Attorney, Agent, or Firm* — Tarolli, Sundheim, Covell & Tummino LLP

(57) ABSTRACT

Devices, systems, and methods for treating cardiac arrhythmia are disclosed herein. In some embodiments, devices, systems, and methods disclosed herein deliver interrogating energy to tissue at a position on a wall of an anatomical structure of a patient. If the devices, systems, and methods disclosed herein detect a change in electrical activity of the anatomical structure in response to the interrogating energy, the devices, systems, and methods disclosed herein can apply irreversible therapy to the tissue. In some embodiments, the change in electrical activity corresponds to slowing or termination of a detected arrhythmia.

22 Claims, 11 Drawing Sheets

Related U.S. Application Data

(60) Provisional application No. 62/965,747, filed on Jan. 24, 2020.

(51) Int. Cl.

| | |
|---|---|
| *A61B 5/287* | (2021.01) |
| *A61B 5/367* | (2021.01) |
| *A61B 18/14* | (2006.01) |
| *A61B 34/10* | (2016.01) |
| *A61B 34/20* | (2016.01) |
| *A61B 18/00* | (2006.01) |
| *A61B 18/02* | (2006.01) |

(52) U.S. Cl.
CPC ........ *A61B 5/6852* (2013.01); *A61B 18/1206* (2013.01); *A61B 34/10* (2016.02); *A61B 34/20* (2016.02); *A61B 2018/0022* (2013.01); *A61B 2018/00351* (2013.01); *A61B 2018/00577* (2013.01); *A61B 2018/00839* (2013.01); *A61B 2018/0212* (2013.01); *A61B 2034/105* (2016.02)

(58) Field of Classification Search
CPC .. A61B 2018/00839; A61B 2018/0066; A61B 2018/00815; A61B 2018/00351; A61B 2018/00267
See application file for complete search history.

(56) References Cited

U.S. PATENT DOCUMENTS

| | | | |
|---|---|---|---|
| 5,376,105 | A | 12/1994 | Hedberg |
| 5,584,885 | A | 12/1996 | Hirschberg et al. |
| 5,995,871 | A | 11/1999 | Knisley |
| 6,190,382 | B1 | 2/2001 | Ormsby et al. |
| 6,292,695 | B1 | 9/2001 | Webster |
| 6,428,537 | B1 * | 8/2002 | Swanson ............ A61B 18/1492 606/41 |
| 6,640,135 | B1 | 10/2003 | Salo et al. |
| 9,131,982 | B2 * | 9/2015 | VanScoy ............ A61B 18/1492 |
| 9,814,521 | B2 | 11/2017 | Geistert |
| 2002/0022866 | A1 | 2/2002 | Borkan |
| 2004/0147920 | A1 * | 7/2004 | Keidar ............... A61B 18/1492 606/41 |
| 2005/0154420 | A1 | 7/2005 | Diaz et al. |
| 2011/0172657 | A1 | 7/2011 | Geistert |
| 2012/0209260 | A1 * | 8/2012 | Lambert ........... A61B 18/1492 606/41 |
| 2013/0006131 | A1 * | 1/2013 | Narayan ............... A61B 5/283 606/32 |
| 2014/0081262 | A1 * | 3/2014 | Koblish ............ A61B 18/1492 606/41 |
| 2016/0022375 | A1 * | 1/2016 | Blake ..................... G16H 50/00 600/424 |
| 2016/0166310 | A1 | 6/2016 | Stewart et al. |
| 2017/0238807 | A9 | 8/2017 | Vertikov |
| 2018/0199990 | A1 * | 7/2018 | Monir ............... A61B 18/1492 |
| 2018/0214202 | A1 | 8/2018 | Howard et al. |
| 2018/0221075 | A1 * | 8/2018 | Warner ................. A61B 18/12 |
| 2018/0325597 | A1 * | 11/2018 | Schwartz ............ A61B 5/0538 |
| 2019/0038349 | A1 * | 2/2019 | Koblish ............... A61B 5/6885 |
| 2020/0205890 | A1 | 7/2020 | Harlev et al. |
| 2020/0359924 | A1 * | 11/2020 | Finlay .................... A61B 5/316 |

OTHER PUBLICATIONS

International Search Report and Written Opinion mailed Jun. 3, 2021; International Patent Application No. PCT/US2021/014216; 21 pages.
ISA, "PCT Application No. PCT/US21/45085, International Search Report and Written Opinion mailed Jan. 20, 2022", 12 pages.
Applicant: Affera, Inc .; "Systems for Cardiac Ablation"; European Application No. EP21744380; Extended European Search Report dated Jan. 12, 2024; 10 pp.

* cited by examiner

SYSTEMS FOR CARDIAC ABLATION AND ASSOCIATED METHODS

CROSS-REFERENCE TO RELATED APPLICATION(S)

This application claims the benefit of International Patent Application No. PCT/US2021/014216, filed Jan. 20, 2021, and U.S. Provisional Patent Application No. 62/965,747, filed Jan. 24, 2020, each of which is incorporated by reference herein in its entirety.

BACKGROUND

Cardiac arrhythmias are usually initiated and/or maintained by specific regions of cardiac tissue. For example, fibrotic or scarred tissue can sometimes cause conduction delay or exhibit automaticity and be responsible for arrhythmia. A minimally-invasive catheter can be used in a patient's heart to treat certain arrhythmias. For example, a minimally-invasive catheter can be used to deliver point-by-point therapy to the wall of the patient's heart. In this scenario, the catheter can be used to form one or more discrete points (e.g., discrete lesions) on the wall of the patient's heart by applying energy (e.g., electrical energy) to the wall. The applied energy damages tissue at the treatment site(s), terminating the tissue's electrical activity. In turn, abnormal electrical signals can be prevented from propagating through the treated tissue, thereby preventing arrhythmias.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

A. Overview

Figure 1:
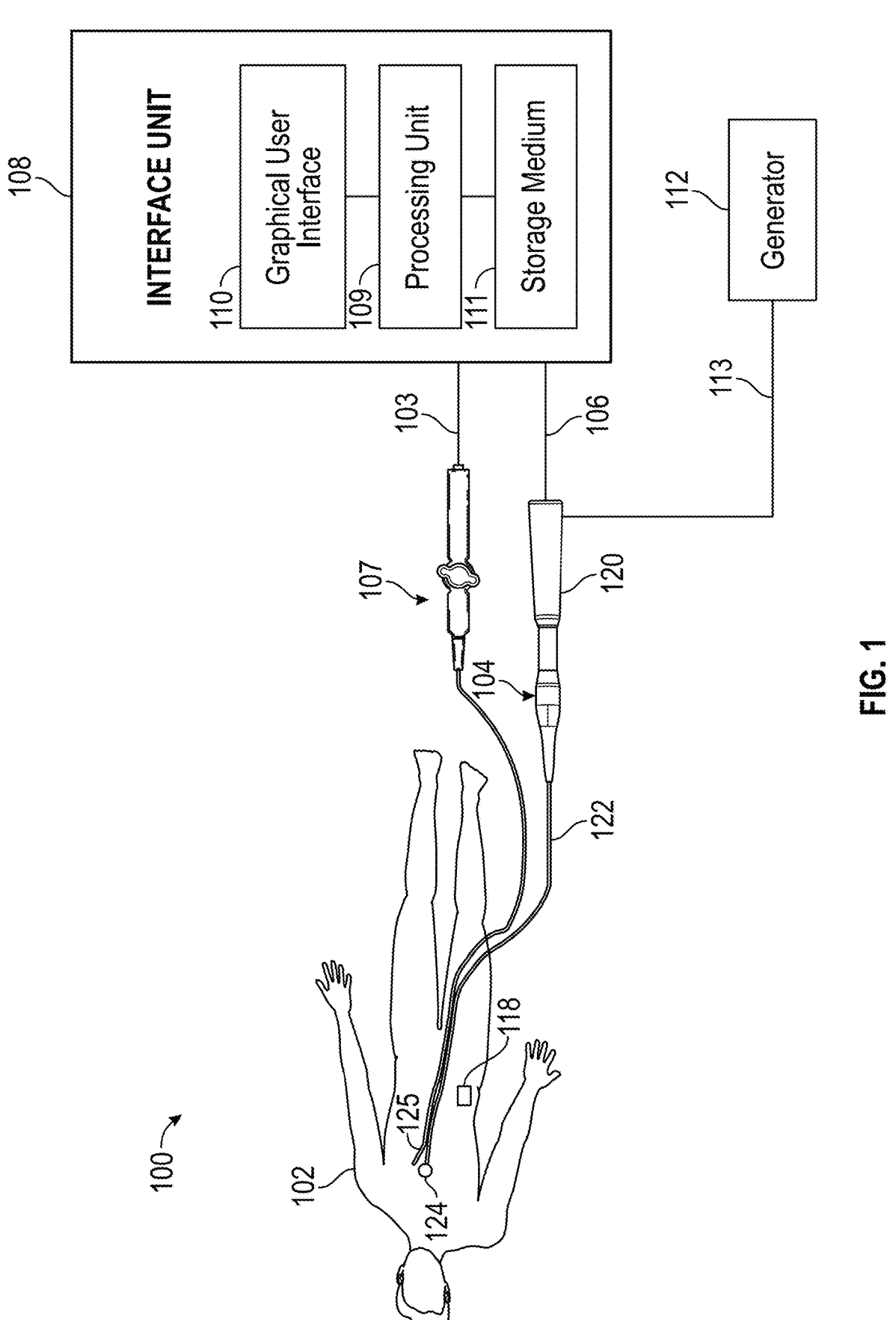
FIG. 1 is a schematic representation of a system for treating a human patient and configured in accordance with various embodiments of the present technology.

As discussed above, a minimally-invasive catheter can be used to apply energy to tissue to damage the tissue and terminate the tissue's electrical activity. In turn, abnormal electrical signals can be prevented from propagating through the treated tissue, thereby preventing arrhythmias. To treat arrhythmias, however, it is often desirable to treat only problematic tissue. That is, it is often undesirable to treat cardiac tissue that does not contribute to an arrhythmia. When patients exhibit arrhythmias, two primary methods are employed to determine locations of problematic tissue: (a) activation mapping and (b) entrainment mapping.

Activation mapping involves determination of excitation timing for various parts of the anatomy. By determining an excitation sequence (or pattern) across multiple parts of the anatomy, a physician can identify the part of the anatomy that is initiating or helping to sustain an arrhythmia. In turn, the physician can deliver therapy to tissue of the identified part to block its electrical conduction, thereby terminating the arrhythmia. Although often effective, activation mapping is time consuming, requires specialized medical equipment, and requires a high level of operator/physician skill. Moreover, in some situations, activation mapping does not provide a clear indication of specific tissue of the part that is initiating or helping to sustain an arrhythmia. Furthermore, some arrhythmias (e.g., atrial tachycardia or atrial fibrillation) may be unstable or may terminate early and may therefore be unmappable. That is, activation mapping assumes aperiodic signals are not mappable.

Entrainment mapping involves tissue pacing/stimulation at various sites within an anatomical structure. Entrainment mapping assumes that tissue in a path of tissue critical to sustaining an arrhythmia will have a post-pacing interval identical or close to the cycle length of the arrhythmia. Entrainment mapping, however, is only able to identify tissue that is on the critical path of tissue; it does not pinpoint an appropriate treatment site. In addition, entrainment mapping assumes that an arrhythmia is a macro-reentrant circuit, rather than a focal source or micro-reentry, and is therefore only useful for mapping a subset of arrhythmias. Moreover, pacing during entrainment mapping may terminate an arrhythmia, rendering it difficult to re-induce and continue investigating the arrhythmia. Furthermore, similar to activation mapping, entrainment mapping can only be used to map stable arrhythmias.

In contrast with these conventional techniques, the present disclosure is directed to devices, systems, and methods that deliver interrogating energy (e.g., reversible pulsed field energy, reversible electroporation, etc.) to tissue at a potential treatment site to determine whether delivering irreversible therapy to the tissue at the potential treatment site would effectively treat an arrhythmia. More specifically, the devices, systems, and methods of the present technology deliver interrogating energy to a potential treatment site within an anatomical structure and measure a corresponding electrical response. Because the interrogating energy temporarily stuns tissue at a potential treatment site, the corresponding electrical response provides a temporary indication of an electrical response that would result if irreversible therapy were delivered to the potential treatment site. If an arrhythmia/excitation pattern of the anatomical structure remains unchanged after delivery of interrogating energy, the devices, systems, and methods of the present technology can determine that tissue at the potential treatment site does not contribute to the measured arrhythmia. In some embodiments, the devices, systems, and methods of the present technology can proceed to investigate another potential treatment site in the manner described above. On the other hand, if an arrhythmia/excitation pattern of the anatomical structure changes after delivery of interrogating energy to tissue at a potential treatment site, the devices, systems, and methods of the present technology can proceed to deliver irreversible therapy to the tissue at the potential treatment site to treat the measured arrhythmia.

Specific details of several embodiments of the present technology are described herein with reference to FIGS. 1-11. Although many of the embodiments are described with respect to devices, systems, and methods of applying interrogating energy to tissue in a heart of a patient to determine appropriate treatment sites for treating an arrhythmia with irreversible therapy, other applications and other embodiments in addition to those described herein are within the scope of the present technology. For example, unless otherwise specified or made clear from context, the devices, systems, and methods of the present technology can be used for any of various medical procedures, such as procedures performed on a hollow anatomical structure of a patient, and, more specifically, in a hollow anatomical structure in which direct visual access to the medical procedure is impractical and/or is improved by the use of a model of the anatomical structure. Thus, for example, the systems, devices, and methods of the present technology can be used to facilitate visualization of a medical device inserted into a heart cavity as part of a medical treatment associated with diagnosis, treatment, or both of a cardiac condition. Additionally, or alternatively, the devices, systems, and methods of the present technology can be used in one or more medical procedures associated within interventional pulmonology, brain surgery, or sinus surgery (e.g., sinuplasty).

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in an anatomical chamber. As used herein, the term "patient" should be considered to include human and/or non-human (e.g., animal) patients upon which a medical procedure is being performed.

B. Selected Embodiments of Cardiac Arrhythmia Treatment Devices, Systems, and Methods 1. Cardiac Arrhythmia Treatment Devices and Systems FIG. 1 is a schematic representation of a system 100 for treating a human patient 102 and configured in accordance with an embodiment of the present technology. In the arrangement shown in FIG. 1, the system 100 is being used to perform a medical procedure (e.g., a diagnosis procedure, an ablation treatment, or both) on the patient 102. The system 100 can include a medical device 104 connected via an extension cable 106 to an interface unit 108. The interface unit 108 (e.g., a catheter interface unit) can include a processing unit 109 (e.g., one or more processors), a graphical user interface 110, and a storage medium 111. The graphical user interface 110 and the storage medium 111 can be in electrical communication (e.g., wired communication, wireless communication, or both) with the processing unit 109. The storage medium 111 can have stored thereon computer executable instructions for causing the one or more processors of the processing unit 109 to carry out one or more portions of the various methods described herein, unless otherwise indicated or made clear from context. The medical device 104 can further be connected via an extension cable 113 to an energy generator 112. The generator 112 can be configured to deliver electrical energy (e.g., radiofrequency energy, pulsed field energy, electroporation energy, etc.) to a tip section 124 of the medical device 104.

In some embodiments, the system 100 can include one or more other components, such as a mapping system, a recording system, an irrigation pump, and/or one or more electrodes 118 attached to the skin of the patient 102 (e.g., one or more return electrodes, one or more electrodes configured to capture an electrocardiogram of the patient 102, etc.). As another example, the system 100 can include a multipolar catheter 107 (e.g., a coronary sinus catheter). The multipolar catheter 107 can be connected via an extension cable 103 to the interface unit 108 and can include a tip portion 125 configured to be inserted into an anatomical structure (e.g., a heart) of the patient 102. As discussed in greater detail below, the multipolar catheter 107 can be configured to capture one or more bipolar electrograms while the tip portion 125 is within the anatomical structure.

The graphical user interface 110 can be used as part of diagnosis and/or treatment of tissue of an anatomical structure (e.g., a heart) of the patient 102 by, for example, generating and/or displaying three-dimensional annotations and/or other information relative to the location of the tip section 124 of the medical device 104. The three-dimensional annotations generated and/or displayed in accordance with various embodiments of the present technology can be used alone or in combination with other three-dimensional information, such as with a three-dimensional surface representation of the anatomical structure. In some embodiments, for example, a three-dimensional annotation can represent the current location of the tip section 124 of the medical device 104 within the anatomical structure and/or the location of the tip section 124 within the anatomical structure when therapy was delivered. In these and other embodiments, three-dimensional annotations can display various information based, at least in part, on signals received from sensors 126 distributed about the tip section 124 of the medical device 104. In this manner, the present technology is expected to provide a physician with improved spatial context for three-dimensional movement and/or proximity of the medical device 104 relative to one or more surfaces of the anatomical structure. As a specific example, generating and/or displaying the three-dimensional annotations and/or other information alone or in combination with the three-dimensional model on the graphical user interface 110 during therapy according to any one or more of the methods described herein can facilitate three-dimensional movement of the medical device 104 within the anatomical structure to investigate potential treatment sites for irreversible therapy delivery and/or to create one or more lesions in a desired pattern on one or more surfaces of the anatomical structure represented by the three-dimensional model.

Figure 2:
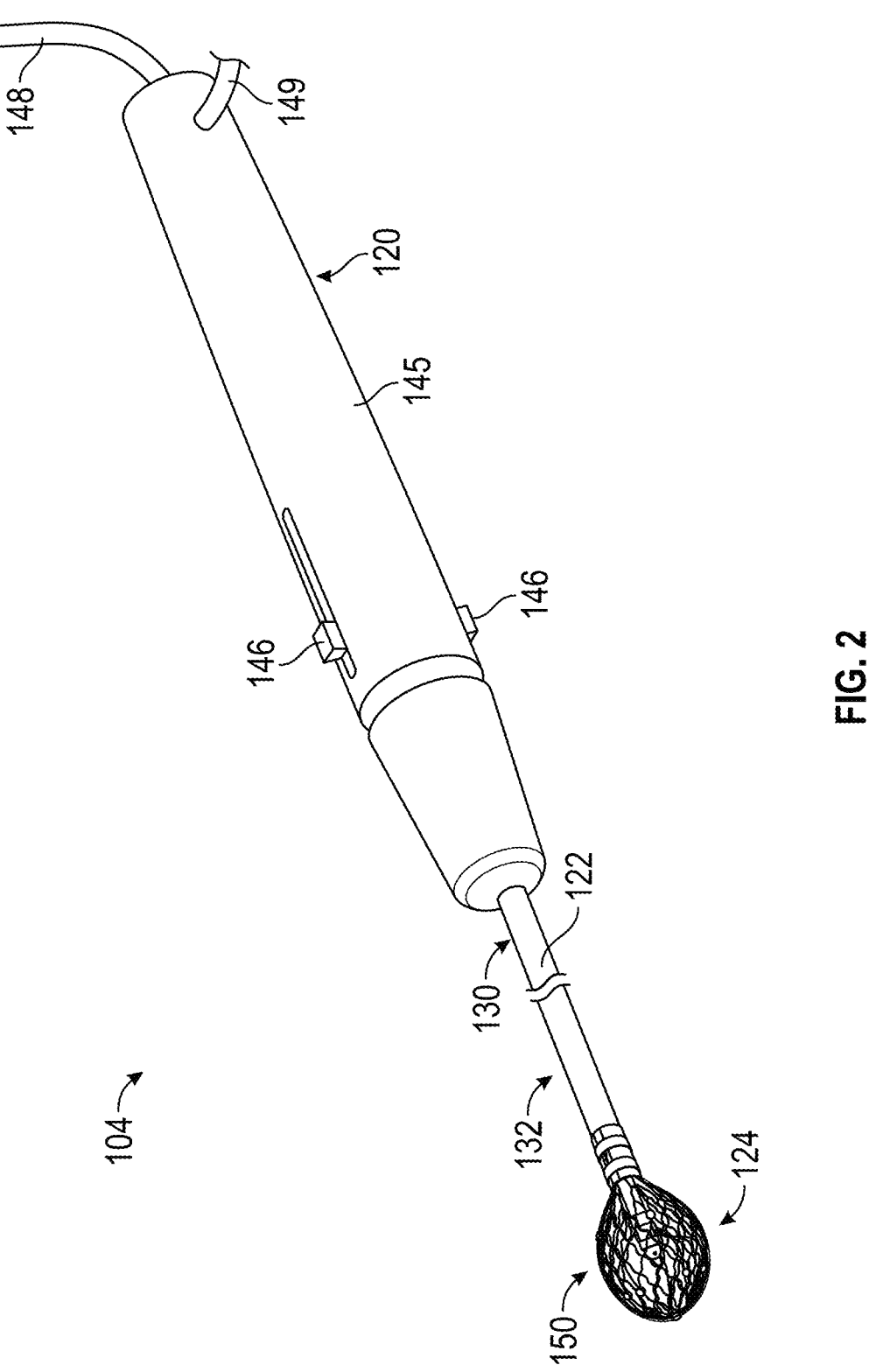
FIG. 2 is a perspective view of an exemplary medical device of the system of FIG. 1 configured in accordance with various embodiments of the present technology.
Figure 3:
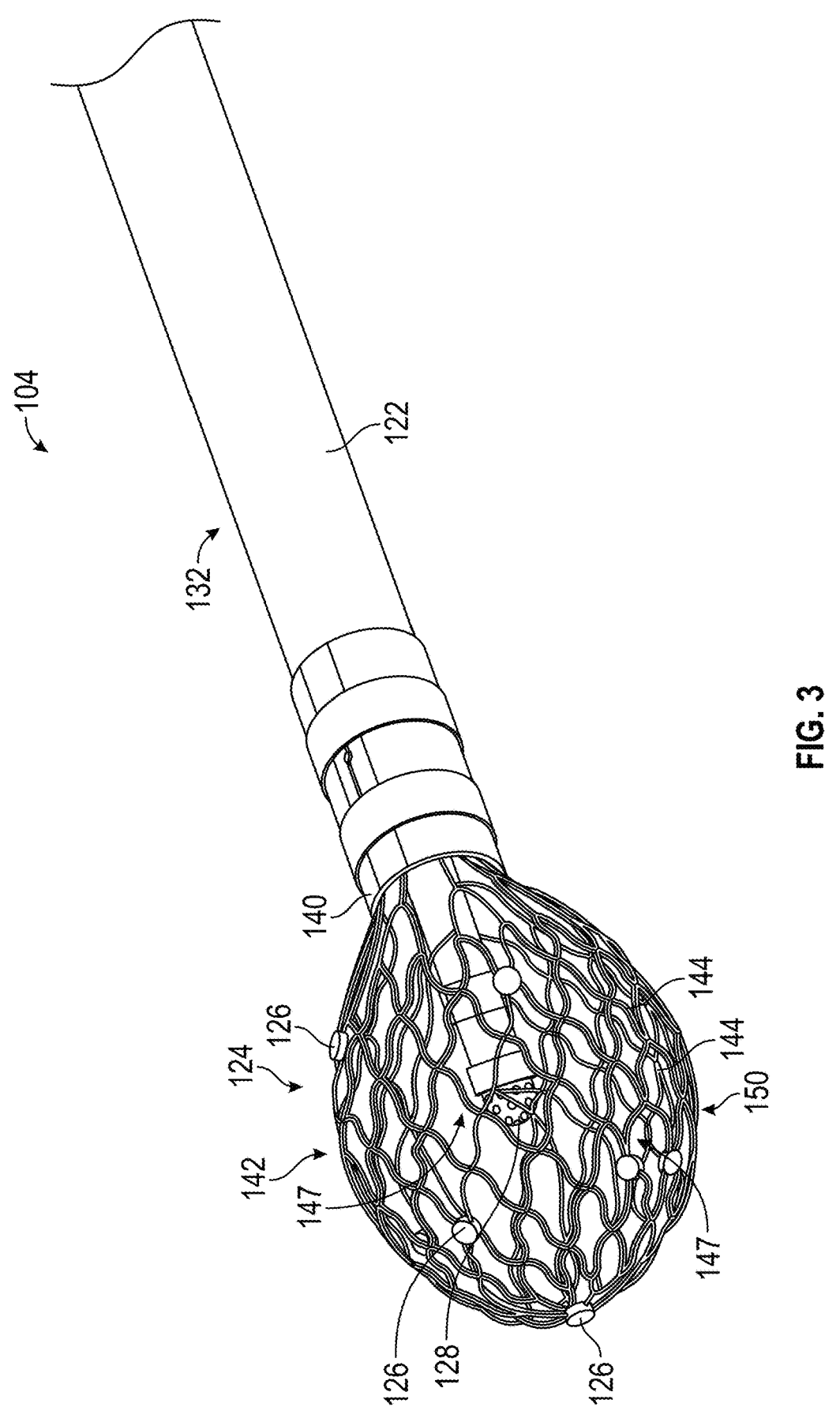
FIG. 3 is a schematic representation of a tip section of the medical device of FIG. 2 and configured in accordance with various embodiments of the present technology.

FIG. 2 is a perspective view of the medical device 104 of the system 100 of FIG. 1, and FIG. 3 is a schematic representation of a tip section 150 of the medical device 104. Referring to FIGS. 1-3 together, the medical device 104 can be any of various different medical devices known in the art (e.g., for diagnosis, treatment, or both). In the illustrated embodiment, for example, the medical device 104 is a catheter. The medical device 104 can include a handle 120, a shaft 122, a tip section 124, and/or an irrigation element 128. The handle 120 can be coupled to a proximal end portion 130 of the shaft 122. The tip section 124 and/or the irrigation element 128 can be coupled to a distal end portion 132 of the shaft 122 opposite the proximal end portion 130. In some embodiments, the shaft 122 can define a lumen that can be in fluid communication with a fluid delivery device such as an irrigation pump (not shown). Additionally, or alternatively, the shaft 122 can include electrical wires extending along the shaft 122 to carry signals between the tip section 124 and the handle 120.

The handle 120 can include a housing 145 and an actuation portion 146. In use, the actuation portion 146 can be operated to deflect a distal end portion 132 of the shaft to facilitate positioning the tip section 124 into contact with tissue at a treatment site. The handle 120 can further be coupled to a fluid line connector 149 and/or to an electrical connector 148 for delivery of irrigation fluid, electrical signals, and/or energy (e.g., electrical energy), respectively, along the shaft 122 to/from the tip section 124 (e.g., to/from an electrode 150 and/or to/from one or more sensors 126 of the tip section 124).

The tip section 124 generally includes any portion of the catheter 104 that directly or indirectly engages tissue for the purpose of treatment, diagnosis, or both and, therefore, can include all manner and type of contact and/or non-contact interaction with tissue known in the art. For example, the tip section 124 can include contact and/or non-contact interaction with tissue in the form of energy interaction (e.g., electrical energy, ultrasound energy, light energy, and any combinations thereof) and further, or instead, can include measurement of electrical signals emanating from tissue. Thus, for example, the tip section 124 can deliver energy (e.g., electrical energy) to tissue in the anatomical structure as part of any number of procedures including treatment (e.g., ablation, electroporation, etc.), diagnosis (e.g., mapping), or both.

In the illustrated embodiments, the tip section 124 includes a coupling portion 140 and a deformable portion 142. As used herein, the terms "expandable" and "deformable" are used interchangeably, unless otherwise specified or made clear from the context. Thus, for example, it should be understood that the deformable portion 142 is expandable unless otherwise specified. The coupling portion 140 is secured to the distal end portion 132 of the shaft 122, and the deformable portion 142 can extend distally from the coupling portion 140.

The deformable portion 142 of the tip section 124 can be deformed for delivery and expanded at a treatment site to have a cross-sectional dimension larger than a cross-sectional dimension of the shaft 122. Further, in an expanded state, the deformable portion 142 of the tip section 124 is deformable upon sufficient contact force with tissue. As described in greater detail below, the shape and extent of the deformation of the deformable portion can be detected based at least in part on signals received from sensors 126 of the tip section 124. In some embodiments, the deformable portion 142 can be radiopaque such that deformation of the deformable portion 142 as a result of contact with tissue is observable, for example, through X-ray or similar visualization techniques. The detection and/or observation of the deformation of the deformable portion 142 of the tip section 124 can, for example, provide improved certainty that an intended treatment is, in fact, being provided to tissue. It should be appreciated that improved certainty of positioning of an electrode 150 with respect to tissue can reduce the likelihood of gaps in a lesion pattern and, also or instead, can reduce the time and number of lesions otherwise required to avoid gaps in a lesion pattern.

The deformable portion 142 of the tip section 124 can include an electrode 150 (e.g., an ablation electrode, an electroporation electrode, etc.). In some embodiments, the deformable portion 142 can include struts 144 joined together to form the electrode 150. In the illustrated embodiment, the struts 144 are joined to collectively define a plurality of cells 147. In other embodiments, however, the struts 144 can be joined in accordance with methods known in the art. Additionally, or alternatively, at least some of the struts 144 can be coupled to the coupling portion 140 of the tip section 124 to secure the deformable portion 142 to the distal end portion 132 of the shaft 122. The struts 144 can be moveable relative to one another. More specifically, the struts 144 can be flexible to one another such that the deformable portion 142 can move between a compressed state, in the presence of external force, and an uncompressed state, in the absence of external force (e.g., in embodiments where the deformable portion 142 is self-expandable).

In general, the struts 144 of the electrode 150 can be dimensioned and arranged relative to one another for delivery of substantially uniform current density through the deformable portion 142 of the tip section 124. The struts 144 can be electrically coupled to the electrical connector 148 (e.g., via one or more wires (not shown) extending along the shaft 122).

The electrode 150 is a continuous structure about the deformable portion 142 that acts as one electrode in a monopolar electrode configuration. It should be appreciated, however, that the electrode 150 can include electrically isolated portions about the deformable portion 142 such that the electrode 150 includes two electrodes of a bipolar electrode configuration. In use, energy (e.g., electrical energy, radiofrequency (RF) energy, etc.) can be delivered to the electrode 150 to ablate or otherwise treat (e.g., via irreversible electroporation) tissue (e.g., in contact with the electrode 150). As compared to smaller electrodes, the electrode 150 can provide wider lesions, facilitating the creation of a pattern of overlapping lesions (e.g., reducing the likelihood of arrhythmogenic gaps, and reducing the time and number of lesions required for an overlapping pattern, or both). Additionally, or alternatively, the larger electrode 150 can facilitate the delivery of more power for providing wider and deeper lesions.

In these and other embodiments, the electrode 150 can be an electroporation electrode configured to apply one or more electrical pulses to cells of tissue. For example, the catheter 104 can be configured to apply pulsed field energy (e.g., reversible electroporation, irreversible electroporation, pulsed electrical fields, etc.) and/or another form of energy to tissue at a treatment site via the electrode 150 of the tip section 124. As a more specific example, the catheter 104 can be configured to deliver monophasic or biphasic pulses with high voltage (e.g., between about 500 volts and 4000 volts) and short duration (e.g., between 100 nanoseconds and 200 microseconds) to the electrode 150.

Additionally, or alternatively, the catheter 104 can be configured to deliver various forms of pulse trains of energy to tissue at a treatment site via the electrode 150 of the tip section 124. For example, the catheter 104 can deliver energy to tissue either continuously or as a train of tightly (e.g., temporally) spaced pulses followed by a suspension period during which no energy is delivered to the tissue. At the end of the suspension period, the catheter 104 can again deliver energy to tissue either continuously or as a train of tightly spaced pulses followed by another suspension period. The catheter 104 can repeat this cycle as needed. In still other embodiments, the catheter 104 can vary the amount of current delivered during either continuous energy delivery or during delivery of different pulses (e.g., pulses of a pulse train).

As best seen in FIG. 3, the tip section 124 and/or the deformable portion 142 can include one or more sensors 126. For example, the tip section 124 can include one or more of electrodes, thermocouples, thermistors, ultrasound transducers, optical fibers, image sensors, and/or other types of sensors. In use, the sensors 126 can be used in one or more modes of parameter measurement. For example, the sensors 126 can measure temperature, electrogram characteristics (e.g., amplitude), force, acoustic properties, impedance, location (e.g., motion during therapy), shape of the deformable portion 142 (e.g., during deployment or deformation), shape of an anatomical structure, energy (e.g., power, voltage, current, impedance), and/or other parameter measurements. These parameters vary over time, producing time-varying signals that can be measured by the interface unit 108.

Sensors 126 can be mounted about (e.g., along) the deformable portion 142 of the tip section 124 (e.g., mounted onto one of the struts 144 of the deformable portion 142) and can be electrically insulated from the electrode 150. In general, the sensors 126 can be positioned along one or both of the inner portion and the outer portion of the deformable portion 142. For example, sensors 126 can extend through a portion of the deformable portion 142. Such positioning of the sensors 126 through a portion of the deformable portion 142 can facilitate measuring conditions along the outer portion and the inner portion of the electrode 150 and/or of the deformable portion 142. As a specific example, one or more of the sensors 126 can include a flexible printed circuit, a thermistor secured between portions of the flexible printed circuit, and a termination pad opposite the thermistor. A sensor 126 can be mounted on the deformable portion 142 of the tip section 124 with the thermistor disposed along an outer portion of the deformable portion 142 and the termination pad disposed along the inner portion of the deformable portion 142. In certain instances, the thermistor can be disposed along the outer portion to provide an accurate indication of tissue temperature.

The sensors 126 can be substantially uniformly spaced from one another (e.g., in a circumferential direction and/or in an axial direction) about the deformable portion 142 when the deformable portion 142 is in an uncompressed state. Such substantially uniform distribution of the sensors 126 can, for example, facilitate determining an accurate deformation and/or temperature profile of the deformable portion 142 during use. In some embodiments, one or more sensors 126 can include a radiopaque portion and/or a radiopaque marker to facilitate visualization (e.g., using fluoroscopy) of the sensor 126 during use.

In these and other embodiments, one or more sensors 126 of the medical device 104 (e.g., of the tip section 124) can further be a magnetic position sensor. The magnetic position sensor can be any of various magnetic position sensors well known in the art and can be positioned at any point along the distal end portion 132 of the shaft 122 and/or at any point along the tip section 124. The magnetic position sensor can, for example, include one or more coils that detect signals emanating from magnetic field generators. One or more coils for determining position with five or six degrees of freedom can be used. The magnetic field detected by the magnetic position sensor can be used to determine the position and/or orientation of the tip section 124 and/or of the distal end portion 132 of the shaft 122 according to one or more methods commonly known in the art such as, for example, methods based on using a magnetic sensor to sense magnetic fields and using a look-up table to determine location of the magnetic position sensor. Accordingly, because the tip section 124 is coupled to the distal end portion 132 of the shaft 122 in a known, fixed relationship to the magnetic position sensor, the magnetic position sensor can also provide the location of the tip section 124. While the location of the tip section 124 is described as being determined based on magnetic position sensing, other position sensing methods can additionally or alternatively be used. For example, the location of the tip section 124 can be additionally, or alternatively, based on impedance, ultrasound, and/or imaging (e.g., real time MRI or fluoroscopy). Furthermore, a location of the tip section 124 should be understood to include, for example, a smoothed and/or filtered position and/or orientation.

In some embodiments, one or more wires (not shown) extend from each sensor 126 within or along the inner portion of the deformable portion 142 and into the shaft 122. The one or more wires can be in electrical communication with the interface unit 108 (FIG. 1) such that each sensor 126 can send electrical signals to and receive electrical signals from the interface unit 108 during use. In this regard, one or more sensors 126 can act as an electrode (e.g., a surface electrode) to detect electrical activity of an anatomical structure in an area local to the sensor 126. For example, each sensor 126 can form part of an electrode pair useful for detecting contact between each sensor 126 and tissue. For example, electrical energy (e.g., current) can be driven through each sensor 126 and another electrode (e.g., any one or more of various different electrodes described herein), and a change in a measured signal (e.g., voltage or impedance) can be indicative of the presence of tissue. Because the position of the tip section 124 is known, detection of contact through respective measured signals at the sensors 126 can be useful for determining portions of the deformable portion 142 proximate to tissue and/or for determining a shape of an anatomical structure in which the tip section 124 is disposed during the course of a medical procedure.

In use, each sensor 126 can, further or instead, act as an electrode to detect electrical activity of an anatomical structure local to the respective sensor 126, with the detected electrical activity forming a basis for an electrogram with the respective sensor 126 and, further or instead, can provide lesion feedback. The sensors can be arranged such that electrical activity detected by each sensor 126 can form the basis of unipolar electrograms and/or bipolar electrograms. Additionally, or alternatively, the sensors 126 can cooperate with a center electrode, for example, to provide near-unipolar electrograms. For example, a sensor 126 can be disposed along the irrigation element 128 and can act as the center electrode. Additionally, or alternatively, the irrigation element 128 can act as a center electrode itself. In these and still other embodiments, one or more other sensors can be disposed along the irrigation element 128, such as one or more image sensors.

As discussed above, the medical device 104 can include an irrigation element 128. As best seen in FIG. 3, for example, in the illustrated embodiment the irrigation element 128 can be coupled to the distal end portion 132 of the shaft 122 and can define one or more irrigation holes in fluid communication with the fluid line connector 149 (FIG. 2) via the lumen of the shaft 122 and the handle 120. Accordingly, irrigation fluid can pass through the lumen defined by the shaft 122 and can exit the irrigation element 128 through the irrigation holes.

The irrigation element 128 can include a substantially hemispherical distal portion to facilitate directing irrigation fluid toward substantially the entire inner portion of the deformable portion 142. It should be appreciated, however, that the irrigation element 128 can be any of various different shapes that facilitate multi-directional dispersion of irrigation fluid toward the inner portion of the deformable portion 142. Moreover, the irrigation element 128 can be spaced relative to the inner portion of the deformable portion 142 such that the irrigation holes direct irrigation fluid toward the inner portion of the deformable portion 142 in an expanded state. In particular, given that the deformable portion 142 of the tip section 124 in some embodiments is intended to contact tissue during ablation, the irrigation holes can be oriented toward the inner portion of the deformable portion 142 in contact with the tissue. In certain implementations, the irrigation holes can be spaced circumferentially about and axially along the irrigation element 128. For example, the irrigation holes can be spatially distributed along the irrigation element 128 with at least a portion of the irrigation holes arranged to direct irrigation fluid in a distal direction with respect to the tip section 124 and at least a portion of the irrigation holes arranged to direct irrigation fluid in a proximal direction with respect to the tip section 124. More generally, the irrigation holes can be distributed to produce a relatively uniform dispersion of irrigation fluid along the inner portion of the deformable portion 142 enveloping the irrigation element 128. Directing the irrigation fluid toward the deformable portion 142 of the tip section 124 in this way can, for example, reduce the likelihood of unintended tissue damage resulting from an ablation treatment.

2. Three-Dimensional Models of Anatomical Structures

In certain implementations, the delivery of energy from the tip section 124 to tissue can rely upon proximity between the tip section 124 and the tissue. In such implementations, it may be particularly desirable for the graphical user interface 110 to display a three-dimensional model of the medical device 104 (e.g., of the tip section 124) and/or an anatomical structure to provide the physician with knowledge of the position of the tip section 124 relative to one or more surfaces of the anatomical structure. It should be further appreciated that the devices, systems, and methods of the present disclosure can be implemented using any number and manner of designs of the medical device 104 that rely upon, or at least derive some benefit from, knowledge of location of the tip section 124 relative to one or more surfaces of the anatomical structure.

Referring to FIGS. 1-5 together, a three-dimensional representation 532 (FIG. 5) of an anatomical structure 432 (e.g., an anatomical cavity, such as a heart cavity) of the patient 102 can be constructed based on known positions of the tip section 124 of the medical device 104 in the anatomical structure 432 (e.g., prior to, during, and/or after application of energy to tissue of the anatomical structure 432) and additionally, or alternatively, based on images (e.g., segmented CT or MR images) of the anatomical structure 432 (FIG. 4) acquired prior to or during the procedure. For example, if the tip section 124 of the medical device 104 is movable in blood in the anatomical structure 432 and obstructed only by a surface 433 (FIG. 4) of the anatomical structure 432, the known positions of the tip section 124 of the medical device 104 can be taken together to provide an indication of a blood-tissue boundary of the anatomical structure 432, and this blood-tissue boundary can form a basis for the three-dimensional representation 532 of the anatomical structure 432. In some embodiments, the three-dimensional representation 532 can be a triangular mesh or non-uniform rational basis spline surface.

In general, a three-dimensional model 544 (FIG. 5) can be projected onto the graphical user interface 110. The three-dimensional model 544 can include the three-dimensional representation 532 of the anatomical structure 432 and/or a representation 504 (FIG. 5) of the medical device 104. The representation 504 of the medical device 104 can include, for example, a depiction of the tip section 124 at a location and orientation determined based on signals received from sensors 126 (e.g., from a magnetic position and/or other sensors) distributed about the tip section 124. By way of example and not limitation, the representation 504 can include one or more of the following: an icon; an outline; a two-dimensional geometric shape such as a circle; and a three-dimensional geometric shape such as a sphere. Additionally, or alternatively, the representation 504 of the medical device 104 can include a three-dimensional depiction of the tip section 124. Continuing with this example, the three-dimensional representation 504 of the tip section 124 can be at least partially based on knowledge of the size and shape of the tip section 124. Thus, for example, in implementations in which the deformable portion 142 of the tip section 124 is deformed through contact with a surface of an anatomical structure, the deformation of the deformable portion 142 can be shown in the three-dimensional representation 504 of the tip section 124.

It should be appreciated that the three-dimensional model 544 has utility as, among other things, an analog for the position of the tip section 124 of the medical device 104 in the anatomical structure 432. That is, the position and orientation of the tip section 124 of the medical device 104 relative to the surface 433 of the anatomical structure 432 is known (e.g., based on signals received by the interface unit 108 from sensors 126, such as from a magnetic position sensor) and can be represented on the graphical user interface 110 at a corresponding position and orientation within the three-dimensional representation 532 of the anatomical structure 432. Thus, for example, as the tip section 124 moves within the anatomical structure 432 during a medical procedure, the representation 504 of the medical device 104 can be depicted on the graphical user interface 110 as undergoing analogous, or at least similar, movements relative to the three-dimensional representation 532 of the anatomical structure 432 in the three-dimensional model 544. Given this correspondence between the three-dimensional model 544 and the physical aspects of the medical procedure, it should be appreciated that displaying images of the three-dimensional model 544 on the graphical user interface 110 can be a useful visualization tool for the physician as the physician moves the tip section 124 of the medical device 104 in the anatomical structure 432.

Figure 4:
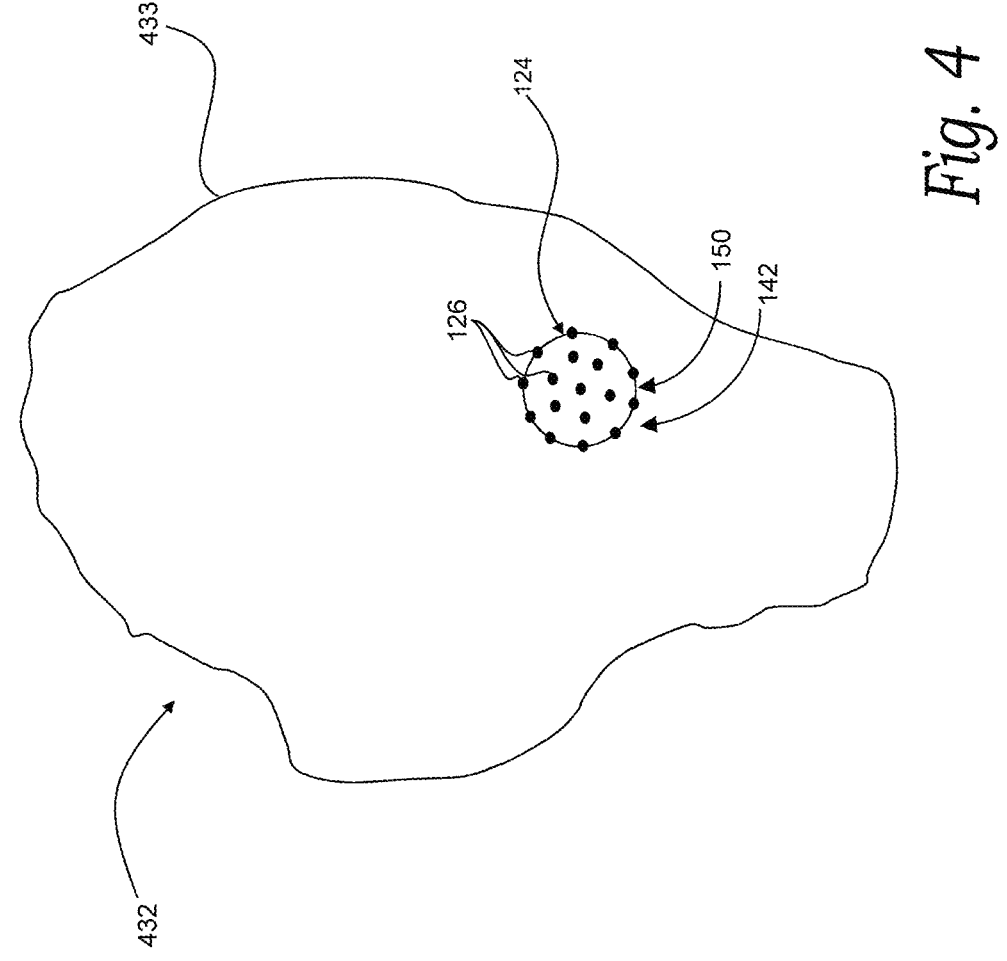
FIG. 4 is a schematic representation of a medical device within an anatomical structure of a patient in accordance with various embodiments of the present technology.
Figure 5:
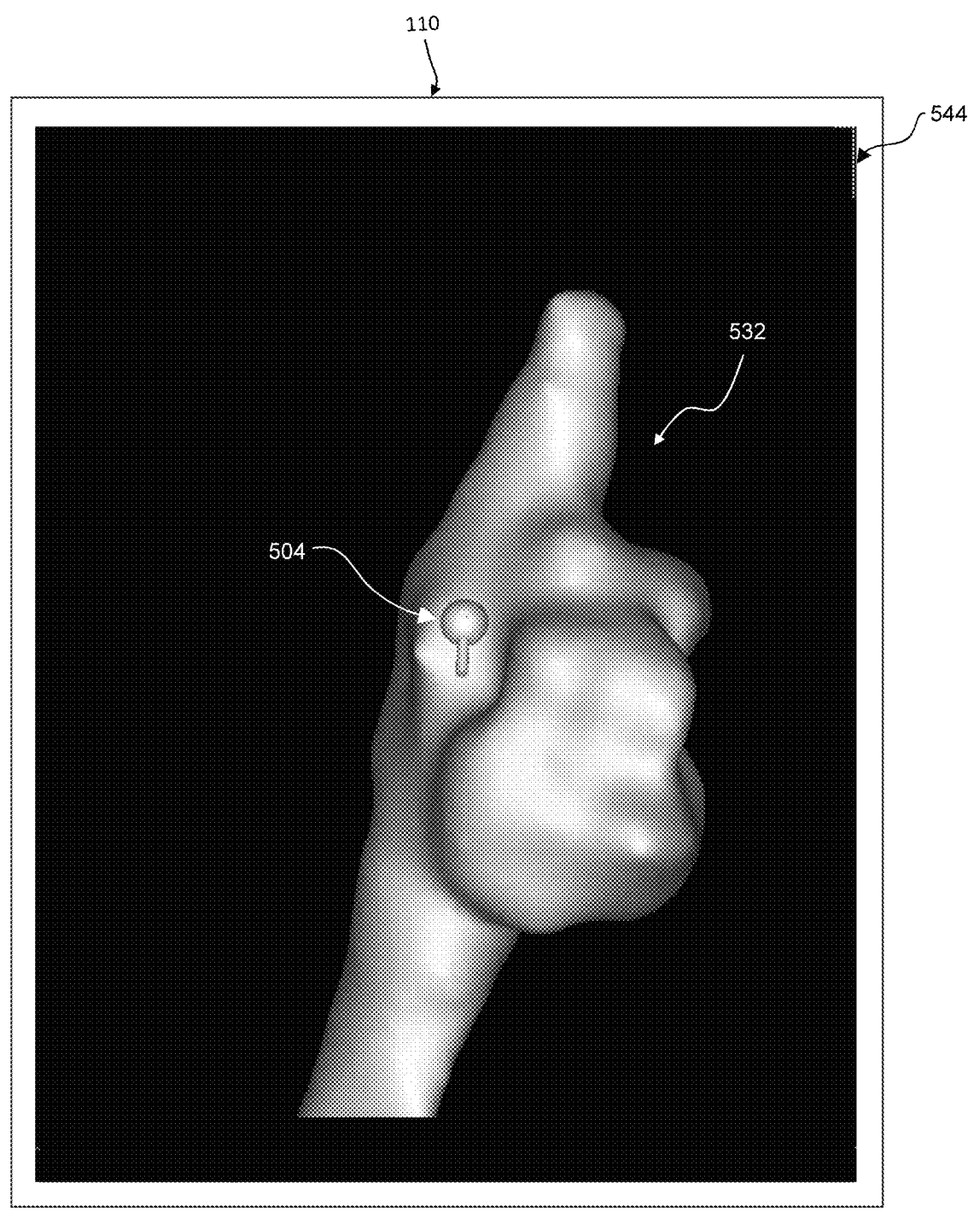
FIG. 5 is a graphical user interface of the system of FIG. 1 displaying a projection of a three-dimensional model during a medical procedure and configured in accordance with various embodiments of the present technology.

As best seen in FIGS. 4 and 5, in one specific treatment example, the tip section 124 can be placed adjacent to the surface 433 of the anatomical structure 432 and energy (e.g., RF energy, electrical energy, etc.) can be directed from the electrode 150 of the tip section 124 to the surface 433 of the anatomical structure 432 to ablate or otherwise treat (e.g., deliver reversible electroporation therapy to) tissue at a treatment site. In implementations in which the anatomical structure 432 is a heart structure, such treatment along the surface 433 of the anatomical structure 432 can, for example, treat cardiac arrhythmia in patients with this condition. However, the effectiveness of the lesions created using the tip section 124 along the surface 433 of the anatomical structure 432 can be dependent upon the location of the lesions. Accordingly, the multi-dimensional visualization of the position of the medical device 104 (facilitated by displaying images of the three-dimensional model 544 according to any one or more of the methods described herein) can be useful for the efficient and effective mapping of the heart and/or efficient and effective delivery of ablation treatment to treat cardiac arrhythmia.

3. Associated Methods

Figure 6:
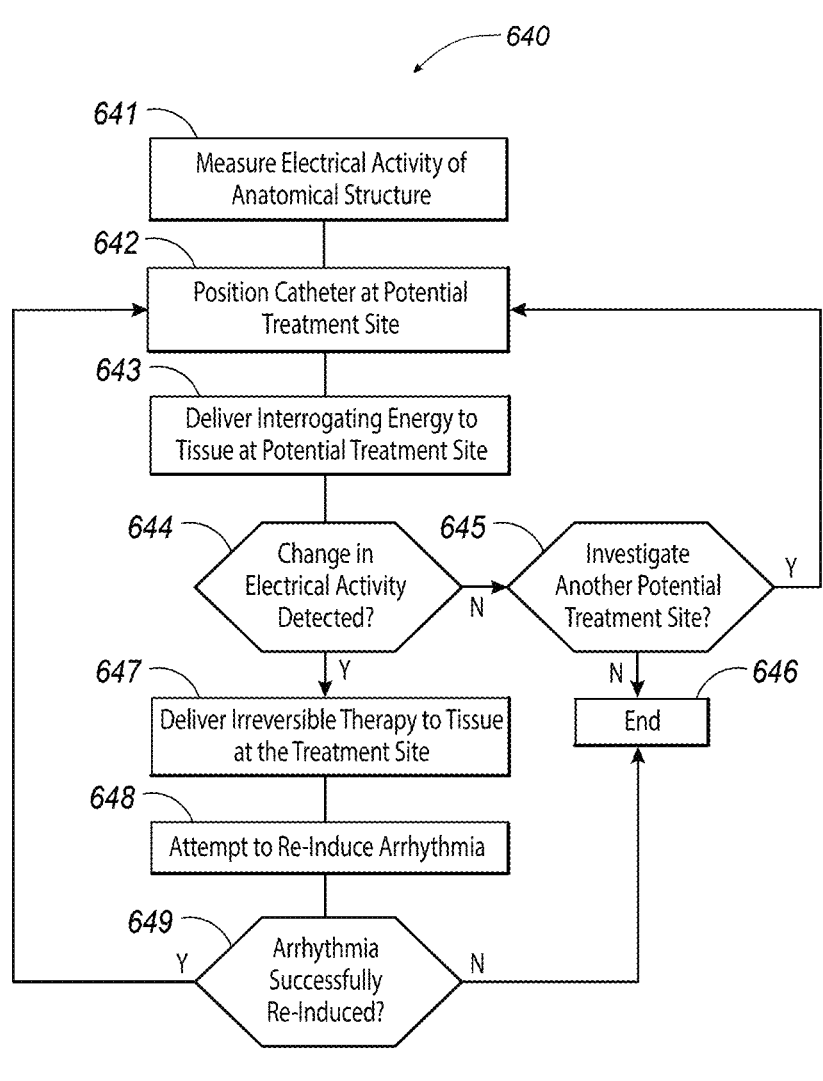
FIG. 6 is a flow diagram illustrating a method for determining a treatment site and/or for treating cardiac arrhythmia within an anatomical structure of a patient in accordance with various embodiments of the present technology.

FIG. 6 illustrates a method 640 for determining a treatment site and/or for treating cardiac arrhythmia within an anatomical structure of a patient in accordance with various embodiments of the present technology. All or a subset of the steps of the method 640 can be executed by various components or devices of a medical system, such as the system 100 illustrated in FIGS. 1-3 or other suitable systems. For example, all or a subset of the steps of the method 640 can be executed by (i) components or devices of an interface unit (e.g., the interface unit 108) and/or (ii) components or devices of a medical device (e.g., the medical device 104). Furthermore, any one or more of the steps of the method 640 can be executed in accordance with the discussion above. Moreover, for the sake of clarity and explanation, FIG. 6 is discussed below in conjunction with FIGS. 7-9.

Figure 7:
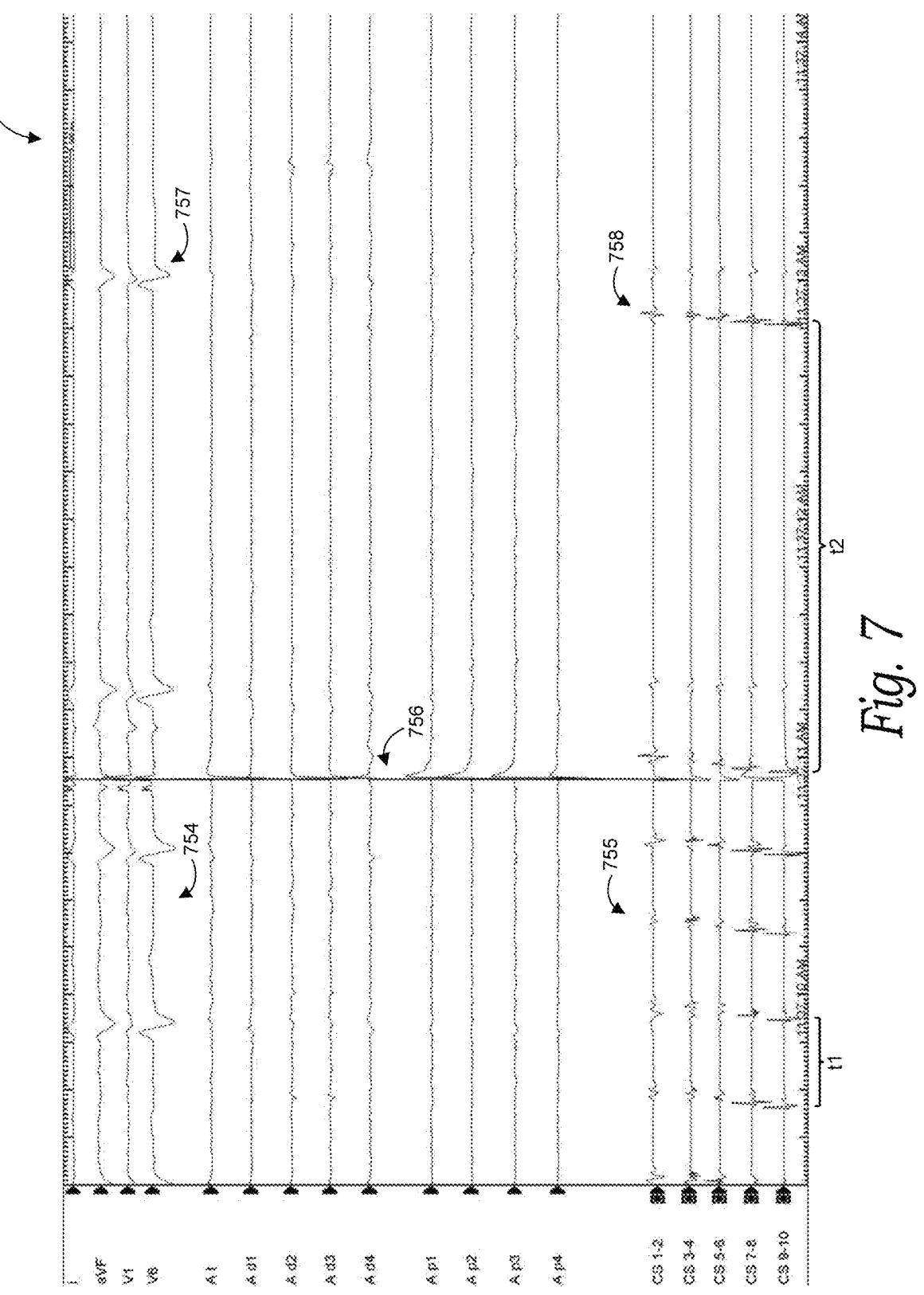
FIGS. 7 and 8 are line plots of measured electrical signals of an anatomical structure of a patient in accordance with various embodiments of the present technology.
Figure 8:
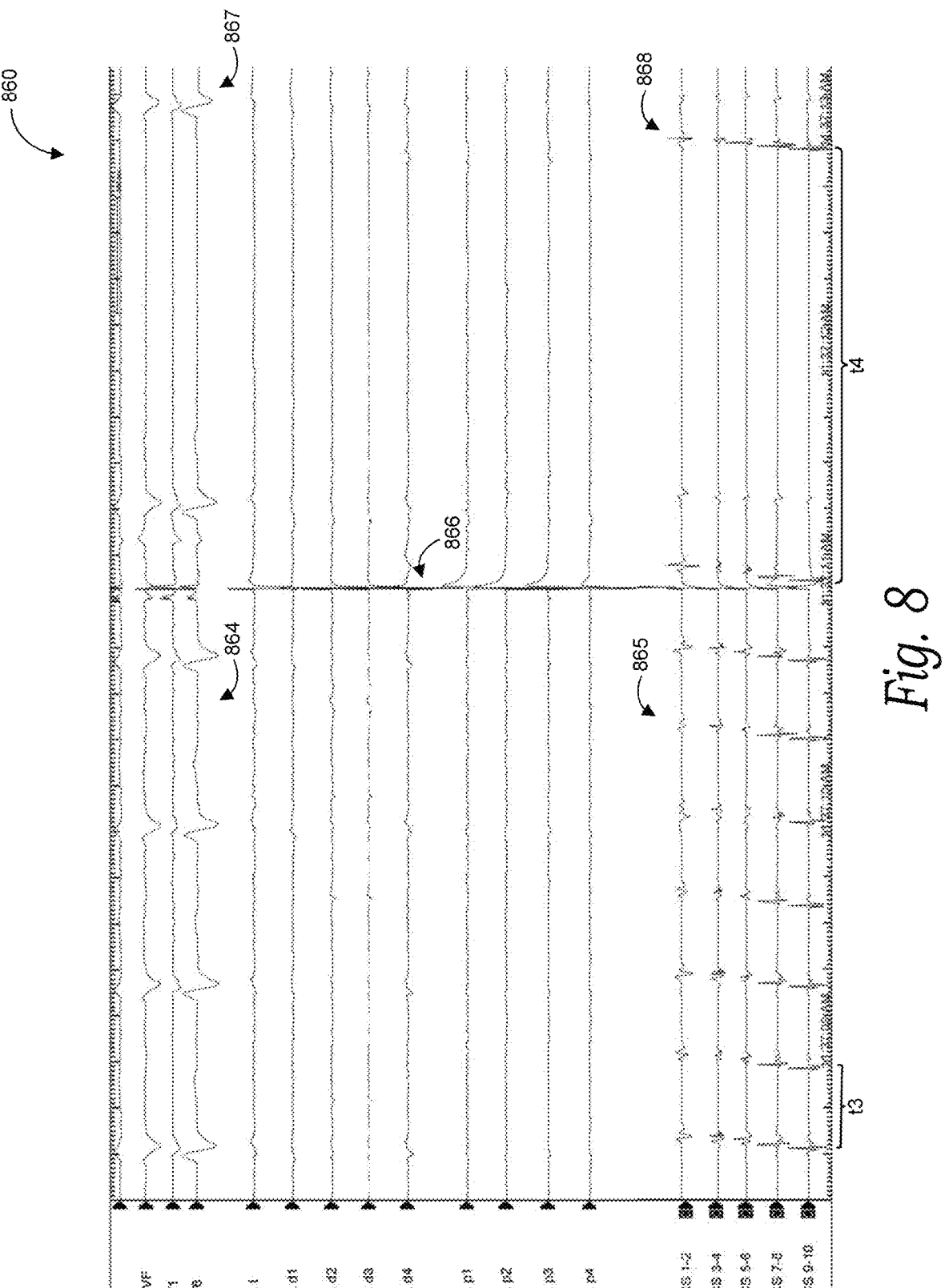

The method 640 begins at block 641 by measuring electrical activity of an anatomical structure of a patient. In some embodiments, the method 640 includes measuring electrical activity of the anatomical structure by capturing an ECG of the anatomical structure (e.g., using electrodes externally attached to the skin of the patient). Additionally, or alternatively, the method 640 includes measuring electrical activity of the anatomical structure by capturing one or more monopolar or bipolar electrograms using an intracardiac reference (e.g., a catheter, a multipolar catheter, a coronary sinus catheter, etc. inserted within the anatomical structure). For example, FIGS. 7 and 8 are line plots 750 and 860, respectively, of measured electrical signals of an anatomical structure of a patient captured in accordance with various embodiments of the present technology. Referring to FIG. 7, the line plot 750 includes three ECG signals aVF, V1, and V6 captured using electrodes externally attached to the skin of the patient. The line plot 750 further includes five bipolar electrograms CS 1-2, CS 3-4, CS 5-6, CS 7-8, and CS 9-10 captured using five electrode pairs of a multipolar catheter positioned within the anatomical structure. In some embodiments, the method 640 can display all or a subset of the measured electrical signals on a graphical user interface.

The measured electrical signals provide an indication of electrical activity of the anatomical structure and can be used by the method 640 to detect and/or display when the anatomical structure of the patient is exhibiting an arrhythmia. For example, the line plot 750 of FIG. 7 illustrates a cardiac arrhythmia in sections 754 and 755 having a cycle length of approximately 360 ms. Similarly, the line plot 860 of FIG. 8 illustrates a cardiac arrhythmia in sections 864 and 865 having a cycle length of approximately 350 ms. In some embodiments, the method 640 can detect and/or display an arrhythmia when adjacent voltage peaks in a cardiac signal captured by an ECG electrode and/or by the intracardiac reference are separated by a period of time (e.g., a cycle length t1 illustrated in FIG. 7 and/or a cycle length t3 illustrated in FIG. 8) that differs from (e.g., is less than or greater than by a predetermined amount) a typical period of time separating adjacent voltage peaks during normal sinus rhythm for the patient or another group of patients.

In some embodiments, the method 640 includes measuring electrical signals as the anatomical structure spontaneously exhibits an arrhythmia. In these and other embodiments, the method 640 can induce an arrhythmia in the anatomical structure and measure the resultant electrical signals. For example, the method 640 can stimulate tissue in the anatomical structure using a pacing catheter or other device. In these and still other embodiments, the method 640 can continuously or periodically measure electrical signals emanating from the anatomical structure (e.g., for the duration of the method 640, only during specific steps of the method 640, etc.).

At block 642, the method 640 next includes positioning a catheter at a potential treatment site. In some embodiments, the catheter is configured to deliver reversible and/or irreversible therapy to tissue on the wall of the anatomical structure. For example, the catheter can be the catheter 104 of FIGS. 1-3. In these and other embodiments, the method 640 can determine a location of a tip section of the catheter within the anatomical structure and/or verify contact/proximity of the tip section to target tissue using one or more magnetic position sensors, electrical signals (e.g., impedance) measured by sensors distributed about the tip section of the catheter, ultrasound navigation, and/or other imaging means (e.g., fluoroscopy).

In some embodiments, the potential treatment site is any site along the wall of the anatomical structure. For example, the potential treatment site can be any site within the anatomical structure that the movable catheter has yet to visit and/or investigate. In these and other embodiments, the potential treatment site is a site within an identified area of interest of the anatomical structure. For example, an area of interest can be identified by performing activation mapping or entrainment mapping prior to performing the method 640. In these embodiments, the method 640 can investigate only potential treatment sites within the identified area of interest rather than investigating potential treatment sites throughout the entire anatomical structure.

At block 643, the method 640 includes investigation of the potential treatment site by delivering interrogating energy to tissue at the potential treatment site. In some embodiments, the method delivers interrogating energy to tissue using the catheter positioned at the potential treatment site. For example, the catheter can be positioned against and deliver interrogating energy to tissue at a single location at the potential treatment site. As another example, the catheter can be positioned against and deliver interrogating energy to tissue at multiple locations at the potential treatment site (e.g., to stun a greater area of tissue with the interrogating energy). Continuing with this example, the method 640 can reposition the catheter and deliver the interrogating energy to tissue at each of the multiple locations within a specified period of time (e.g., within a few seconds, before tissue at any one of the multiple locations fully recovers or recovers to a specified extent, etc.). In embodiments in which the catheter is the catheter 104 of FIGS. 1-3, the method 640 can deliver interrogating energy to tissue via the electrode 150 and/or one or more sensors 126 distributed about the tip section 124 of the catheter 104. In these and other embodiments, the interrogating energy delivered to tissue can be monopolar (e.g., delivered between an electrode within the anatomical structure and one or more electrode patches externally attached to the skin of the patient) and/or can be bipolar (e.g., delivered between two electrodes positioned within the anatomical structure, such as between two electrodes on the same catheter or between an electrode on two separate catheters).

The interrogating energy delivered to tissue can be any therapy that temporarily stuns the tissue (e.g., that temporarily hinders or blocks electrical conductivity of the tissue) but that allows the tissue to recover (e.g., without or with minimal permanent injury) within a short period of time (e.g., within a few seconds, minutes, and/or hours). For example, the interrogating energy can be an interrogating pulse of electrical energy or a collection of interrogating pulses of electrical energy. The interrogating pulse can be a monophasic or biphasic electrical signal with high voltage and short duration. It is expected that a biphasic interrogating pulse (in contrast with a monophasic electrical signal) can avoid muscle capture of the anatomical structure, collateral structures, and/or skeletal muscle induced when interrogating energy is delivered to tissue.

In embodiments in which the interrogating pulse is biphasic, each polarity of the interrogating pulse can be symmetric. For example, a biphasic interrogation signal can include delivery of a first polarity of energy (e.g., 1000 volts for 1 μs) followed by delivery of a second polarity of energy (e.g., −1000 volts for 1 μs). In some embodiments, the interrogating pulses is a biphasic signal such that each polarity of the biphasic interrogating pulse contains no less than 80 percent of charge delivered (in aggregate) of the other polarity over a total period of 10 ms or less. As a more specific example, a biphasic interrogation signal can include delivery of a first polarity of energy (e.g., −500 volts for 1 μs), followed by delivery of a second polarity of energy (e.g., 1000 V for 1 μs), followed by delivery of the first polarity of energy (e.g., −500 volts for 1 μs). As another similar example, a biphasic interrogation signal can include delivery of a first polarity of energy (e.g., −1000 volts for 0.5 μs), followed by delivery of a second polarity of energy (e.g., 1000 volts for 1 μs), followed by delivery of the first polarity of energy (e.g., 1000 volts for 0.5 μs). In some embodiments, the interrogating pulse can be any electrical signal crossing at least 1000 volts for at least 100 ns at least once.

In some embodiments, the interrogating signal can be a square wave. In other embodiments, the interrogating signal can have other shapes. For example, the interrogating signal can be a sine function, a root raised cosine, a Gaussian function, a trapezoid, and/or another shaped signal. In these and other embodiments, the interrogating signal is non-thermal. For example, the delivery of the interrogating signal to tissue at the potential treatment site is expected to raise (or lower) the temperature of the tissue at the potential treatment site by less than 1° C.

At block 644, the method 640 determines whether the interrogating energy delivered to tissue at block 643 induced a change in the measured electrical activity of the anatomical structure of the patient. Because interrogating energy delivered to tissue at a potential treatment site temporarily stuns the tissue, the measured electrical activity of the anatomical structure after delivery of interrogating energy to the tissue at the potential treatment site provides a temporary indication of an electrical response that would permanently result if irreversible therapy were delivered to the tissue at the potential treatment site. Thus, if the method 640 detects no change in the electrical activity of the anatomical structure after interrogating energy is delivered to the tissue at the potential treatment site, the method 640 can determine that the tissue at the treatment site is not contributing to an arrhythmia identified and/or displayed in the measured electrical signals at block 641. On the other hand, if the method 640 detects a change in the electrical activity of the anatomical structure after interrogating energy is delivered to the tissue at the potential treatment site (e.g., a prolongation/slowing of the arrhythmia cycle length, or a termination of the arrhythmia), the method 640 can (i) determine that the tissue at the treatment site is contributing to an arrhythmia identified and/or displayed in the measured electrical signals at block 641 and (ii) determine that the potential treatment site is an appropriate treatment site for delivery of irreversible therapy.

In some embodiments, a change in the electrical activity of the anatomical structure indicative of slowing or termination of an arrhythmia identified and/or displayed in the measured electrical signals at block 641 can include a change in signal timing and/or morphology of one or more measuring elements or electrodes. As used herein, "morphology" is the shape of the activation signal in the electrogram, and may be applied to both ECG and to intracardiac EGMs. When associated with intracardiac EGMs, morphology can include amplitude, duration (of the activation), multiple (e.g., double) potentials, and fractionation. Referring to the line plot 750 illustrated in FIG. 7, for example, delivering interrogating energy (shown at section 756 of the line plot 750) to tissue at a potential treatment site resulted in termination of the arrhythmia detected and displayed in sections 754 and 755 of the line plot 750. In particular, the period of time between adjacent voltage peaks in the cardiac signals captured by the ECG electrodes and/or in the bipolar electrograms captured by the intracardiac reference lengthened significantly from cycle length t1 to cycle length t2, indicating that the rhythm of the anatomical structure slowed and sinus rhythm was restored after delivery of the interrogating energy. Following re-induction of arrhythmia by pacing coronary sinus electrodes, referring to the line plot 860 illustrated in FIG. 8, delivering interrogating energy again (shown at section 866 of the line plot 860) to tissue at the same potential treatment site resulted in termination of the arrhythmia detected and displayed in sections 864 and 865 of the line plot 860. In particular, the period of time between adjacent voltage peaks in the cardiac signals captured by the ECG electrodes and/or in the bipolar electrograms captured by the intracardiac reference lengthened significantly from cycle length t3 to cycle length t4, indicating that the rhythm of the anatomical structure slowed and sinus rhythm was restored after delivery of the interrogating energy. In general, the method 640 can determine that tissue at the potential treatment site is contributing to the arrhythmia based on slowing or termination of arrhythmia detected using any of a number of methods known in the art for determination of rhythm and/or cycle length. Additionally, or alternatively, the method 640 can avoid determining that tissue at the potential treatment site is contributing to the arrhythmia if a slowing or termination of arrhythmia is determined to have been caused by an effect other than stunning of tissue at the potential treatment site (e.g., by tissue stimulation due to delivery of the interrogating energy). If the method 640 determines that tissue at the potential treatment site is contributing to the arrhythmias detected in the measured cardiac signals, the method can proceed to block 647 to deliver irreversible therapy to the tissue at the corresponding treatment sites. As discussed in greater detail below with respect to FIG. 9, the method 640 can record the location of the potential treatment site in the anatomical structure and/or can record an indication that tissue at the potential treatment site is likely contributing to the detected arrhythmia.

In contrast, if the method 640 determines that the period of time between adjacent voltage peaks in the measured electrical activity of the anatomical structure is the same (or substantially the same) before and after interrogating energy was delivered to tissue at the potential treatment site, the method 640 can determine that the interrogating energy delivered to the tissue did not slow or terminate a detected arrhythmia. In this scenario, the method 640 can determine that the tissue at the potential treatment site is not contributing to the arrhythmia detected in the measured cardiac signals and can proceed to block 645 to determine whether there are other potential treatment sites to investigate. As discussed in greater detail below with respect to FIG. 9, the method 640 can record the location of the potential treatment site in the anatomical structure and/or can record an indication that tissue at the potential treatment site is not contributing to the detected arrhythmia.

At block 645, the method 640 determines whether there is another potential treatment site to investigate. For example, the method 640 can determine whether there is another potential treatment site that has not been visited and/or investigated within the anatomical structure and/or within an identified area of interest. If the method 640 determines that there are other potential treatment sites to investigate, the method 640 can return to block 642 to position the catheter at a next potential treatment site. Otherwise, the method 640 can terminate at block 646.

At block 644, in the event that the method 640 determines that interrogating energy delivered to tissue at the potential treatment site at block 643 induced a change in the measured electrical activity of the anatomical structure of the patient (e.g., that the interrogating energy delivered to the tissue slowed or terminated a detected arrhythmia), the method 640 proceeds to block 647 to identify the potential treatment site as a treatment site and to apply irreversible therapy to tissue at the treatment site.

At block 647, the method 640 identifies the potential treatment site as an appropriate treatment site for irreversible therapy and/or delivers irreversible therapy to tissue at the appropriate treatment site. Irreversible therapy includes any therapy that permanently damages tissue at the treatment site, decreasing the tissue's electrical activity such that abnormal electrical signals are prevented from propagating through the damaged tissue. Examples of irreversible therapy include pulsed field ablation, radiofrequency (RF) ablation, cryo-ablation, ultrasound ablation, laser balloon ablation, and/or hot balloon ablation. In some embodiments, the method 640 can deliver irreversible therapy comprising monophasic or biphasic pulses of energy with high voltage (e.g., between about 500 volts and 4000 volts) and short duration (e.g., between 100 nanoseconds and 100 microseconds). Additionally, or alternatively, the method 640 can deliver various forms of pulse trains of energy to tissue at a treatment site as irreversible therapy. For example, the method 640 can deliver energy to tissue either continuously or as a train of tightly (e.g., temporally) spaced pulses followed by a suspension period during which no energy is delivered to the tissue. At the end of the suspension period, the method 640 can again deliver energy to tissue either continuously or as a train of tightly spaced pulses followed by another suspension period. The method 640 can repeat this cycle as needed. In still other embodiments, the method 640 can vary the amount of current delivered during either continuous energy delivery or during delivery of different pulses (e.g., pulses of a pulse train). In these and still other embodiments, the method 640 can deliver irreversible therapy to (i) only the tissue at the treatment site and/or (ii) tissue at the treatment site as well as tissue proximate (e.g., surrounding, adjacent, etc.) the treatment site. In some embodiments, the method 640 delivers irreversible therapy to the tissue at the treatment site using the movable catheter and/or the same catheter used to deliver interrogating energy to the tissue at block 643. In other embodiments, the method 640 delivers irreversible therapy to the tissue at the treatment site using a separate catheter from the catheter used to deliver interrogating energy to the tissue at block 643. In some embodiments, the method 640 delivers interrogating energy at block 643 to a first area of tissue on a wall of the anatomical structure that is larger (e.g., greater, at least 1.5 times larger, at least 2 times larger, etc.) than a second area of tissue to which the method 640 delivers irreversible therapy at block 647.

In these and other embodiments, the method 640 can interrogate tissue at multiple potential treatment sites, identify those potential treatment sites where interrogating energy successfully slowed or terminated the detected arrhythmia, and choose all or a subset of the identified potential treatment sites at which to deliver irreversible therapy to corresponding tissue. For example, although applying interrogating energy to tissue at two potential treatment sites slows or terminates a detected arrhythmia, applying interrogating energy to tissue at one of the two potential treatment sites can further slow or more readily terminate the detected arrhythmia than applying interrogating energy to tissue at the other of the two potential treatment sites. Continuing with this example, the method 640 can deliver irreversible therapy to tissue at the one of the two potential treatment sites and refrain from delivering irreversible therapy to tissue at the other of the two potential treatment sites (or vice versa). In some embodiments, the method 640 can deliver irreversible therapy to tissue at both of the two potential treatment sites.

At block 648, the method 640 further includes attempting to re-induce an arrhythmia. For example, the method 640 can attempt to re-induce an atrial arrhythmia by stimulating the atrium from the coronary sinus. In these and other embodiments, the method 640 can attempt to re-induce an arrhythmia by stimulating tissue at or proximate (e.g., surrounding, adjacent, etc.) the tissue treated with irreversible therapy at block 647. In these and still other embodiments, the method 640 can attempt to re-induce an arrhythmia by stimulating any other tissue within the anatomical structure, such as any other tissue within an identified area of interest of the anatomical structure. In some embodiments, the method 640 attempts to re-induced the same arrhythmia that was terminated at blocks 643, 644, and 647. In other embodiments, the method 640 attempts to re-induce a different arrhythmia than the arrhythmia terminated at blocks 643, 644, and 647. In some embodiments, stimulation delivered to the coronary sinus and/or other tissue within the anatomical structure can be an electrical signal having a cycle length (e.g., approximately 200 ms) that is shorter (e.g., faster) than the normal sinus rate of the patient.

At block 649, the method 640 determines whether the method 640 successfully re-induced an arrhythmia at block 648. If the method 640 determines that the method 640 successfully re-induced an arrhythmia in the anatomical structure, the method 640 returns to block 642 to position the movable catheter at a potential treatment site. On the other hand, if the method 640 determines that the method 640 did not successfully re-induce an arrhythmia at block 648, the routine 640 terminates at block 646.

Although the steps of the method 640 are discussed and illustrated in a particular order, the method 640 illustrated in FIG. 6 is not so limited. In other embodiments, the method 640 can be performed in a different order. In these and other embodiments, any of the steps of the method 640 can be performed before, during, and/or after any of the other steps of the method 640. Moreover, a person of ordinary skill in the relevant art will recognize that the illustrated method can be altered and still remain within these and other embodiments of the present technology. For example, one or more steps of the method 640 (e.g., blocks 648 and 649) illustrated in FIG. 6 can be omitted and/or repeated in some embodiments.

In these and still other embodiments, the method 640 can include one or more additional steps than illustrated in FIG. 6. For example, the method 640 can display one or more visual indicia of therapy delivery and/or electrical activity of the anatomical structure on a graphical user interface. That is, it may be particularly desirable for the method 640 to display one or more therapy annotations or tags alone or in combination with a three-dimensional representation of the anatomical structure and/or a representation of one or more medical devices (e.g., the movable catheter and/or the intra-cardiac reference) to provide the physician with various information relating to past and/or present regions of therapy delivery.

In general, as discussed above with respect to FIGS. 1-5, the tip section 124 of the medical device 104 of the present technology can include sensors 126 (e.g., electrogram sensors, temperature sensors, etc.) distributed about the tip section 124. Each of the sensors 126 can provide information pertaining to only an area local to the respective sensor 126. Thus, based at least in part on signals received from one or more of the sensors 126 distributed about the tip section 124, the devices, system, and methods of the present technology can generate and/or display a map of therapy annotations or tags representative of information relevant to a physician, such as (i) information pertaining to (e.g., current or past) locations and/or orientations of the tip section 124; (ii) information regarding proximity between the medical device 104 and the anatomical structure 432 (e.g., which portion of the tip section 124 of the medical device 104 and/or which surface of an anatomical structure are/were in contact and/or close proximity); (ii) information relating to tissue characteristics (e.g., impedance, temperature, etc.) at a location on the anatomical structure; (iii) information (e.g., location, size, shape, orientation, etc.) relating to a lesion formed at a location on an anatomical structure; (iv) information (e.g., power, voltage, current, etc.) regarding energy delivered to a location on an anatomical structure; and/or (v)

other information, such as distance from a nearest therapy site, whether discrete therapy regions overlap and/or are connected, and/or time of therapy delivery (e.g., start time, stop time, how recently therapy was applied to a site, etc.).

Figure 9:
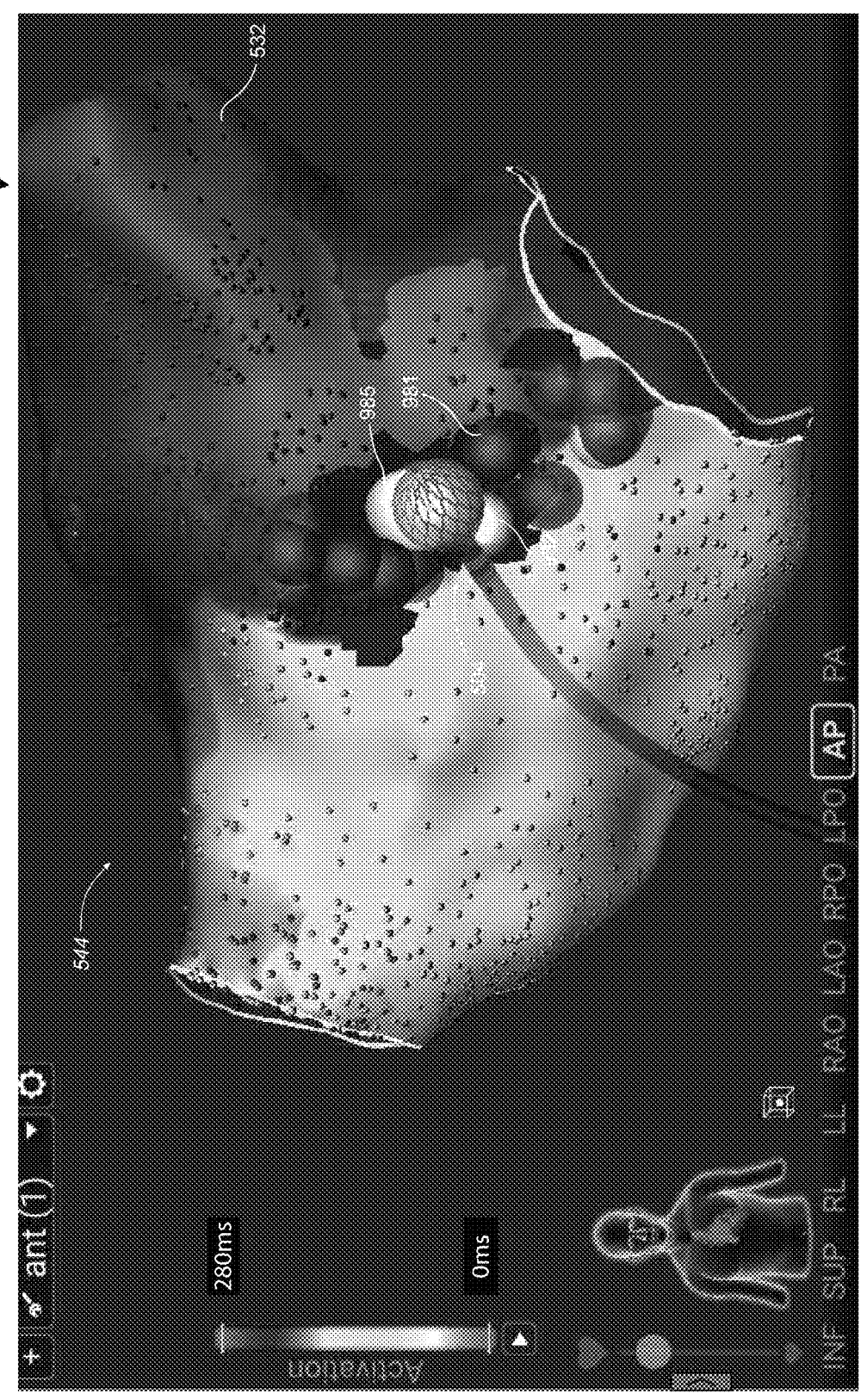
FIG. 9 is an image of a three-dimensional model illustrating various visual indicia that can be generated and/or displayed in accordance with various embodiments of the present technology.

FIG. 9 is an example image 980 of the model 544 of FIG. 5 that the method 640 can display on a graphical user interface in accordance with various embodiments of the present technology. For the sake of efficient and clear description, references in the discussion of FIG. 9 to the medical device 104 and to the anatomical structure 432 refer to features first described and/or discussed above with reference to FIGS. 1-5. As shown in FIG. 9, the method 640 can display the model 544 with the representation 532 of the anatomical structure 432 and/or the representation 504 of the medical device 104. In some embodiments, the representation 504 of the medical device 104 can depict the current location and orientation of the medical device 104 within the anatomical structure 432 in accordance with the discussion above. Thus, for example, as the tip section 124 moves within the anatomical structure 432 during a medical procedure, the representation 504 of the medical device 104 can be depicted on the graphical user interface 110 as undergoing analogous, or at least similar, movements relative to the three-dimensional representation 532 of the anatomical structure 432 in the three-dimensional model 544.

In some embodiments, the representation 532 of the anatomical structure 432 can be pattern-coded and/or color-coded on the display. For example, as shown in FIG. 9, the representation 532 is displayed as an activation map where each pattern and/or color provides an indication of timing of activation of tissue. The activation map can be generated using an activation mapping technique prior to performing the method 640. As discussed in greater detail above, activation mapping suffers several shortcomings. In the illustrated embodiment, for example, the activation map is useful to identify an area of interest that includes tissue that may be contributing to an arrhythmia of the anatomical structure 432. But the activation map is not detailed enough to identify specific locations of contributing or problematic tissue (e.g., narrow channels of slowed conduction). Furthermore, the activation map is not conclusive (i.e., electrical activity of the left atrium of the anatomical structure 432 captured and depicted in the illustrated activation map appears merely as passive activation emanating from the right atrium of the anatomical structure 432 rather than as a macrorcentrant arrhythmia within the left atrium).

To address these concerns, the method 640 of FIG. 6 can display one or more indicia related to therapy delivered to tissue within the anatomical structure 432 to provide a greater amount of information to a physician and a more precise indication of problematic tissue. The one or more indicia can include properties (e.g., size, position, color, pattern, continuity, transparency, etc.) that vary depending on (i) the relative position and/or orientation of the representation 504 of the medical device 104 with respect to the three-dimensional representation 532 of the anatomical structure 432, (ii) the type of therapy delivered, and/or (iii) detected changes in electrical activity after therapy is delivered. For example, as the method 640 delivers interrogating energy to tissue at a potential treatment site at block 643, the method 640 can place a therapy annotation or tag (e.g., a therapy annotation 981) at a position and/or orientation on the representation 532 of the anatomical structure 432 that corresponds to the position and/or orientation of the movable catheter within the anatomical structure 432 when the interrogating energy was applied to the tissue. The therapy annotation 981 can include a first set of properties corresponding to therapy delivered at the potential treatment site. For example, the size of the therapy annotation can correspond to an extent of contact between the tip section of the movable catheter and the wall of the anatomical structure 432. As another example, the shape of the of the therapy annotation 981 can correspond to the type of therapy delivered. Continuing with this example, as the method 640 delivers interrogating energy at block 643 to tissue at a location in the anatomical structure 432 corresponding to the location of the therapy annotation 981 in the representation 532, the method 640 can display the therapy annotation 981 as a sphere to indicate that interrogating energy was delivered to tissue at this location. In contrast, the method 640 can display a therapy annotation 985 as a flat disk or other shape to indicate that the method 640 delivered irreversible therapy at block 647 to tissue at a corresponding location within the anatomical structure 432.

As yet another example, the color or pattern used to display the therapy annotation 981 can provide an indication of whether applying interrogating energy at a corresponding location in the anatomical structure 432 resulted in slowing or termination of an arrythmia. Continuing with this example, the method 640 can display the therapy annotation 981 using a first pattern and/or color (e.g., blue) to indicate that interrogating energy delivered to tissue at a corresponding location within the anatomical structure 432 did not terminate a detected arrhythmia. In contrast, the method 640 can display a therapy annotation 982 using a second patterned and/or colored (e.g., yellowed) globe to indicate that interrogating energy delivered to tissue at a corresponding location within the anatomical structure 432 slowed or terminated a detected arrhythmia. Furthermore, such pattern- or color-coding can vary depending on the type of slowing or termination. For example: (i) if interrogating energy delivered to tissue resulted in little or no slowing (e.g., less than 10 ms change in cycle length), a first pattern and/or color (e.g., blue) can be applied to the therapy annotation 981; (ii) if interrogating energy delivered to tissue resulted in significant slowing (e.g., greater than or equal to 10 ms change in cycle length), a second pattern and/or color (e.g. green) can be applied to the therapy annotation 981; and (iii) if interrogating energy delivered to tissue resulted in termination of the arrhythmia, a third pattern and/or color (e.g. yellow) can be applied to the therapy annotation 981. In some embodiments, the patterns and/or colors used to display one or more of the therapy annotations can based on a function of time. For example, because it is expected that tissue recovers after application of interrogating energy, the patterns, colors, and/or other properties used to display therapy annotations that indicate delivery of interrogating energy can change over time. Continuing with this example, the (i) pattern and/or color used to display the therapy annotation and/or (ii) density, intensity, shade, and/or opacity of a pattern and/or color used to display the therapy annotation can change (e.g., decrease) over time to indicate a predicted extent of tissue recovery at a corresponding location within the anatomical structure 432 after application of interrogating energy.

In some embodiments, the therapy annotations can be generated and/or displayed in substantially real-time. For example, the therapy annotations can be displayed as soon as therapy is delivered to a region of the anatomical structure 432 (or shortly thereafter considering processing time). In these and other embodiments, therapy annotations can be generated and/or displayed during or after the time period in which therapy is delivered to a region of the anatomical structure. Further information regarding therapy annotations, therapy contours, and therapy maps, surfaces, and volumes is provided in International Patent Application No. PCT/US2020/014850, the disclosure of which is incorporated by reference herein in its entirety.

In this manner, a physician is able to view where therapy has been delivered to the anatomical structure 432. In other words, therapy annotations in combination with a representation 532 of the anatomical structure 432 can provide a physician spatial information related to regions of the anatomical structure 432 that have been treated with reversible and/or irreversible therapy, and can aide a physician in specifically identifying problematic tissue that is contributing to a detected arrhythmia.

In some embodiments, one or more steps of the method 640 can be automated. For example, detection of an arrhythmia in measured electrical signals at block 641, delivery of reversible therapy at block 643, determination of whether delivered interrogating energy slowed or terminated a detected arrhythmia at block 644, delivery of irreversible therapy at block 647, re-inducement of an arrhythmia at block 648, determination of whether an arrhythmia has been successfully re-induced at block 649, and/or generation and/or display of therapy annotations can be automatically performed by a computer (e.g., components of the catheter interface unit 108 of FIG. 1). As a more specific example, a computer can automatically deliver irreversible therapy every 1 second as the movable catheter is roved about the anatomical structure 432. In these and other embodiments, the computer can automatically determine whether an instance of delivery of interrogating energy terminated a detected arrhythmia, and/or the computer can automatically generate and/or display a therapy annotation at a corresponding location within the representation 532 having properties that depend on (i) the relative position and/or orientation of the representation 504 of the medical device 104 with respect to the three-dimensional representation 532 of the anatomical structure 432, (ii) the type of therapy delivered, and/or (iii) the detected changes in electrical activity after interrogating energy is delivered.

Figure 10:
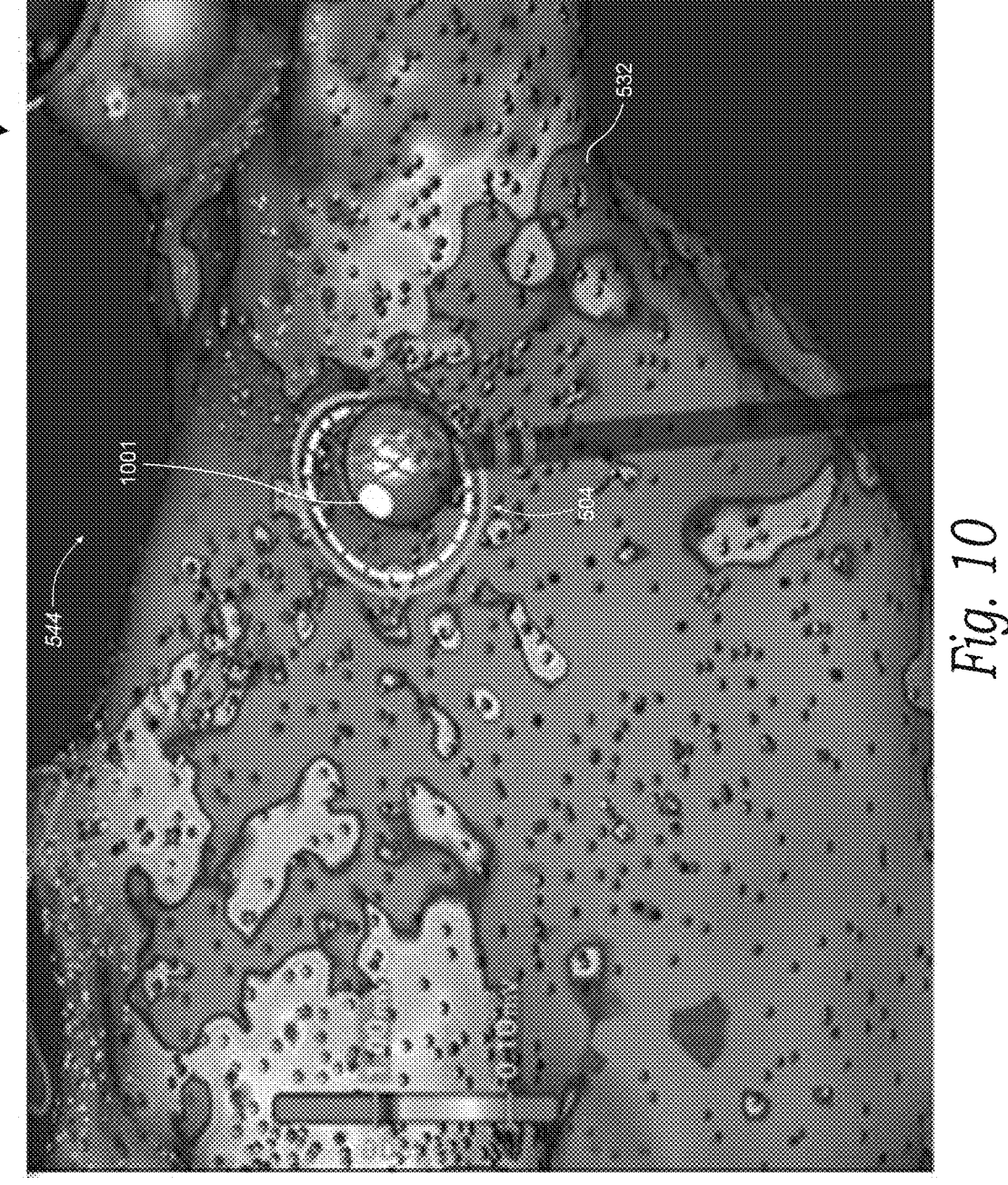
FIG. 10 is an image of a three-dimensional model that can be displayed on a graphical user interface in accordance with various embodiments of the present technology.

FIG. 10 is an image 1000 of the model 544 of FIG. 5 that the method 640 can display on a graphical user interface in accordance with various embodiments of the present technology. For the sake of efficient and clear description, all references in the discussion of FIG. 10 to the medical device 104 and to the anatomical structure 432 refer to features first described and/or discussed above with reference to FIGS. 1-5. As shown in FIG. 10, the method 640 can display the model 544 with the representation 532 of the anatomical structure 432 and/or the representation 504 of the medical device 104. In some embodiments, the representation 504 of the medical device 104 can depict the current location and orientation of the medical device 104 within the anatomical structure 432 in accordance with the discussion above. In the illustrated embodiment, the model 544 depicts the representation 504 of the medical device 104 positioned against and delivering interrogating energy to tissue at a potential treatment site 1001 within the representation 532 of the anatomical structure 432.

Figure 11:
FIG. 11 is a line plot of a plurality of electrograms measuring electrical activity of an anatomical structure of a patient in accordance with various embodiments of the present technology.

FIG. 11 is a line plot 1070 of a plurality of electrograms measuring electrical activity of an anatomical structure of a patient in accordance with various embodiments of the present technology. As shown, the line plot includes an electrogram d2 measuring electrical activity of tissue at the treatment site 1001 of FIG. 10. The electrogram d2 displays the recovery of the tissue every ten seconds after interrogating energy is delivered to the tissue at time t=0. In particular, section 1171 of the electrogram d2 shows a baseline measurement of electrical activity of the tissue with a large amplitude (near-unipolar voltage). The tissue is stunned at time t=0 with interrogating energy, and therefore electrical activity is diminished (amplitude is reduced), as shown in section 1172 of the electrogram d2. Sections 1173-1175 of the electrogram d2 show that the tissue gradually recovers (e.g., electrical activity gradually returns, amplitude increases, etc.) over time until the electrical activity of the tissue at time t=30 (shown in section 1175 of the electrogram d2) is nearly identical to the baseline measurement of electrical activity 30 seconds after the interrogating energy was delivered to the tissue at t=0. It is expected that most tissue recovers within two minutes after delivery of interrogation energy.

C. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively. Moreover, unless the word "or"

is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising." "including." "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A method, comprising:

delivering first energy to first target tissue of an anatomical structure of a patient via an electrode carried by a catheter;

measuring electrical activity of the anatomical structure after delivering the first energy;

analyzing the measured electrical activity to detect a change in an arrhythmia caused by the first energy;

displaying a first therapy annotation in a three-dimensional model of the anatomical structure at a location in the model corresponding to a location of a tip section of the catheter in the anatomical structure when the first energy was delivered to the first target tissue, wherein the first therapy annotation includes a first set of visual properties, and wherein one or more visual properties of the first set are updated dynamically as a function of time to indicate whether the first energy delivered to the first target tissue slowed or terminated the arrhythmia based on the detected change in the arrhythmia and to indicate a predicted extent of recovery of electrical activity of the first target tissue at a given time after delivering the first energy;

delivering second energy to second target tissue of the anatomical structure via the electrode of the catheter, wherein the second target tissue at least partially overlaps with the first target tissue; and

after delivering the second energy, displaying a second therapy annotation in the three-dimensional model of the anatomical structure corresponding to delivery of the second energy to the second target tissue.

2. The method of claim 1 wherein the first set of visual properties includes a color and/or a pattern of the first therapy annotation, and wherein the one or more visual properties include a density, an intensity, a shade, and/or an opacity of the color and/or the pattern.

3. The method of claim 1 wherein the one or more visual properties include a color and/or a pattern of the first therapy annotation.

4. The method of claim 3 wherein the color and/or the pattern of the first therapy annotation include(s):

a first color and/or a first pattern when the first energy delivered to the first target tissue did not slow or terminate the arrhythmia; and a second color and/or a second pattern when the first energy delivered to the first target tissue slowed or terminated the arrhythmia, wherein the second color and/or the second pattern is/are different from the first color and/or the first pattern, respectively.

5. The method of claim 3 wherein the color and/or the pattern of the first therapy annotation include(s):

a first color and/or a first pattern when the first energy delivered to the first target tissue slows a cycle time of the arrhythmia by less than 10 ms; and a second color and/or a second pattern when the first energy delivered to the first target tissue slows the cycle time of the arrhythmia by greater than or equal to 10 ms, wherein the second color and/or the second pattern is/are different from the first color and/or the first pattern, respectively.

6. The method of claim 5 wherein the color and/or the pattern of the first therapy annotation include(s) a third color and/or a third pattern when the first energy delivered to the first target tissue terminates the arrhythmia, and wherein the third color and/or the third pattern is/are different from the first and second colors and/or the first and second patterns, respectively.

7. The method of claim 1 wherein the first set of visual properties includes a size of the first therapy annotation indicative of an extent of contact between the tip section of the catheter and the first target tissue when the first energy was delivered to the first target tissue.

8. The method of claim 1 wherein the first set of visual properties includes a shape of the first therapy annotation indicative of a type of energy of the first energy delivered to the first target tissue.

9. The method of claim 8 wherein the shape of the first therapy annotation includes:

a first shape when the first energy includes stunning energy; and a second shape when the first energy includes ablative energy.

10. The method of claim 1 wherein the first set of visual properties provides an indication of an orientation of the tip section of the catheter relative to the first target tissue when the first energy was delivered to the first target tissue.

11. The method of claim 1 wherein the first set of visual properties provides an indication of which portion of the tip section was contacting the first target tissue when the first energy was delivered to the first target tissue.

12. The method of claim 1 wherein the first set of visual properties provides an indication of characteristics of the first energy delivered to the first target tissue, wherein the characteristics include a voltage level of the first energy delivered to the first target tissue, a current level of the first energy delivered to the first target tissue, a total time the first energy was applied to the first target tissue, or a combination thereof.

13. The method of claim 1 wherein the first set of visual properties provides an indication of a type of energy of the first energy delivered to the first target tissue.

14. The method of claim 1 wherein displaying the first therapy annotation includes generating and/or displaying the first therapy annotation in real time as the first energy is delivered to the first target tissue.

15. The method of claim 1 wherein delivering the first energy comprises delivering stunning energy to the first target tissue.

16. The method of claim 1 wherein delivering the first energy comprises delivering ablative energy to the first target tissue.

17. The method of claim 1 wherein delivering the second energy comprises delivering ablative energy to the second target tissue.

18. The method of claim 1 wherein delivering the second energy comprises delivering stunning energy to the second target tissue.

19. The method of claim 1, further comprising detecting, prior to delivering the first energy to the first target tissue, the arrhythmia based at least in part on electrical signals measured using the tip section of the catheter, a multipolar catheter separate from the catheter, or a combination thereof.

20. The method of claim 1 wherein displaying the second therapy annotation includes displaying the second therapy annotation with a second set of visual properties that provides an indication of whether delivering the second energy to the second target tissue reinduced the arrhythmia.

21. The method of claim 1 wherein displaying the second therapy annotation includes displaying the second therapy annotation at a location in the model corresponding to a location of the tip section of the catheter in the anatomical structure when the second energy was delivered to the second target tissue.

22. A method comprising:

delivering reversible energy to target tissue of an anatomical structure of a patient via an electrode carried by a catheter, wherein the reversible energy temporarily alters electrical activity of the target tissue;

displaying a therapy annotation in a three-dimensional model of the anatomical structure at a location in the model corresponding to a location of a tip section of the catheter in the anatomical structure when the reversible energy was delivered to the target tissue, wherein the therapy annotation includes one or more visual properties; and changing at least one of the one or more visual properties of the therapy annotation as a function of time, wherein the at least one visual property is indicative of a predicted extent of recovery of the electrical activity of the target tissue at a given time after delivering the reversible energy to the target tissue.

* * * * *